(12) United States Patent
Thiem

(10) Patent No.: US 8,383,402 B2
(45) Date of Patent: Feb. 26, 2013

(54) TRICHOPLUSIA NI CELL LINE AND METHODS OF USE

(75) Inventor: Suzanne M. Thiem, Okemos, MI (US)

(73) Assignee: Board of Trustees of Michigan State University, East Lansing, MI (US)

(*) Notice: Subject to any disclaimer, the term of this patent is extended or adjusted under 35 U.S.C. 154(b) by 0 days.

(21) Appl. No.: 12/937,767

(22) PCT Filed: Apr. 14, 2009

(86) PCT No.: PCT/US2009/040554
§ 371 (c)(1),
(2), (4) Date: Dec. 27, 2010

(87) PCT Pub. No.: WO2009/137242
PCT Pub. Date: Nov. 12, 2009

(65) Prior Publication Data
US 2011/0091890 A1    Apr. 21, 2011

Related U.S. Application Data

(60) Provisional application No. 61/044,729, filed on Apr. 14, 2008.

(51) Int. Cl.
*C12N 5/07* (2010.01)
*C12N 5/00* (2006.01)
*C12N 15/00* (2006.01)

(52) U.S. Cl. ............... 435/348; 435/325; 435/320.1

(58) Field of Classification Search .................. None
See application file for complete search history.

(56) References Cited

U.S. PATENT DOCUMENTS

| | | | |
|---|---|---|---|
| 4,745,051 A | | 5/1988 | Smith et al. |
| 6,033,903 A | * | 3/2000 | Sisk et al. ............... 435/320.1 |
| 6,403,375 B1 | * | 6/2002 | Granados .................. 435/348 |
| 2002/0142346 A1 | | 10/2002 | Nestor |
| 2005/0112678 A1 | | 5/2005 | Yang |
| 2005/0123563 A1 | | 6/2005 | Doranz et al. |
| 2010/0249022 A1 | * | 9/2010 | Clapham et al. ............. 514/3.8 |

FOREIGN PATENT DOCUMENTS

| | | |
|---|---|---|
| WO | WO02061087 A2 | 8/2002 |
| WO | WO-2009137242 A2 | 11/2009 |

OTHER PUBLICATIONS

Kopatz et al., AY429106, submitted Nov. 3, 2003.*
Merten, O.W., "Attention with virus contaminated cell lines". Cytotechnology 55:1-2 (2007).
Clontech, GST—Tag Purification Resins. Retrieved from the Internet: <URL: http://www.clontech.com/products/details.asp?product_id=10594>, downloaded Jan. 4, 2009.
"International Application Serial No. PCT/US2009/040554, International Search Report and Written Opinion mailed Jun. 18, 2009", 8 pgs.

Akermoun, M, et al., "Characterization of 16 human G protein-coupled receptors expressed in baculovirus-infected insect cells", Protein Expr. Purif., 44, (2005), 65-74.
Becker, G W, et al., "Characterization by Electrospray Mass-Spectrometry of Human Ca2+-Sensitive Cytosolic Phospholupase-a(2) Produced in Baculovirus_infected Insect Cells", Bio-Technology, 12, (1994), 69-74.
Chai, H, et al., "Insect cell line dependent gene expression of recombinant human tumor necrosis factor", Enzyme Microb. Technol., 18, (1996), 126-132.
Davis, T R, et al., "Baculovirus Expression of Alkalien-Phosphatase as a Reporter Gene for Evaluation of Production, Glycosylation and Secretion", Bio-Technology, 10, (1992), 1148-1150.
Davis, T R, et al., "Comparative Recombinant Protein-Porduction of 8 Insect-Cell Lines", In Vitro Cell. Dev. Biol.-Anim., 29A, (1993), 388-390.
Gaw, Z, et al., "Tissue Culture methods for cultivation of virus grasserie", Acta Virol., 3 (Suppl.), (1959), 55-60.
Grace, T, "Establishment of four strains of cells from insect tissues grown in vitro.", Nature (London), 195, (1962), 788-789.
Granados, R R, et al., "A New Insect-Cell Line from *Trichoplusia ni* (Bti-Tn-5bl-4) Susceptible to *Trichplusia ni* Single Enveloped Nuclear Polyhedrosis-Virus", J. Invertebr. Pathol., 64, (1994), 260-266.
Grisshammer, R Tate, "C.G. Overexpression of Integral Membrane-Proteins for Structural Studies", Quarterly Reviews of Biophysics, 28, (1995), 315-422.
Hollister, J, et al., "Engineering the Protein N-Glycosylation Pathway in Insect Cells for Production of Biantennary, Complex N-Glycans", Biochemistry, 41, (2002), 15093-15104.
Lu, A, et al., "Species-specific effects of the hcf-1 gene on baculovirus virulence", J. Virol., 70, (1996), 5123-5130.
Lukow, V A, et al., "High level expression of non-fused foreign genes with *Autographa californica* nuclear polyhedrosis virus expression vectors", Virology, 170, Lucow, V. A. and Summers, M. D., (1989), 31-39.
Massotte, D, "G protein-coupled receptor overexpression with the baculovirus-insect cell system: a tool for structural and functional studies", Biochim, Biophys. Acta-Biomembr., 1610, (2003), 77-89.
McCusker, E C, et al., "Heterologous GPCR expression: A bottleneck to obtaining crystal structures", Biotechnol. Prog., 23, (2007), 540-547.
McKenna, K A, et al., "Establishment of new *Trichoplusia ne* cell lines in serum free medium for Baculovirus and recombinant protein production", J. Invertebr. Pathol., 71, (1998), 82-90.

(Continued)

*Primary Examiner* — Shulamith H Shafer
(74) *Attorney, Agent, or Firm* — Schwegman Lundberg & Woessner, P.A.

(57) ABSTRACT

An isolated cell from the cell line identified as TnT4. This cell may be infected with a baculovirus expression vector which may carry a heterologous nucleotide that encodes a polypeptide, such as a membrane protein, e.g., human neurotensin receptor 1. Also included is a method for using this cell line to produce a polypeptide, such as a membrane protein; and a method for identifying a cell-of-interest which expresses a protein-of-interest.

19 Claims, 14 Drawing Sheets

OTHER PUBLICATIONS

Ng, G Y.K, et al., "Human Serotonin (1b) Receptor Expression in Sf9 Cells—Phosphorylation, Palmitoylation, adn Adenylyl-Cyclase Inhibition", Biochemistry, 32, (1993), 11727-11733.

Ng, G Y.K, et al., "Phosphorylation and Palmitoylation of the Human D2(L) Dopamine-Receptor in Sf9 Cells", J. Neurochem., 63, (1994), 1589-1595.

Ogonah, O W, et al., "Isolation and characterization of an insect cell line able to perform complex N-linked glycosylation on recombinant proteins", Bio-Technology, 14, (1996), 197-202.

Palomares, L A, et al., "Novel insect cell line capable of complex N-glycosylation and sialylation of recombinant proteins", Biotechnol. Prog., 19, (2003), 185-192.

Sarramegna, V, et al., "Heterologous expression of G-protein-coupled receptors: comparison of expression systems from the standpoint of large-scale production and purification", Cellular and Molecular Life Sciences, 60, (2003), 1529-1546.

Smith, G E, et al., "Modification and Secretion of Human Interleukin-2 Produced in Insect Cells by a Baculovirus Expression Vector", Proceedings of the National Academy of Sciences of the United States of America, 82, (1985), 8404-8408.

Vaughn, J L, et al., "Establishment of 2 Cell Lines from Insect *Spodoptera-frugiperda* (Lepidoptera-Noctuidae)", In Vitro—Journal of the Tissue Culture Association, 13, (1977), 213-217.

Weyer, U, et al., "Analysis of Very Late Gene-Expression by *Autographa-california* Nuclear Polyhedrosis-Virus and the Further Development of Multiple Expression Vectors", J. Gen. Virol., 71, (1990), 1525-1534.

Wickham, T J, et al., "Screening of Insect Cell-Lines for the Production of Recombinant Proteins and Infectious Virus in Baculovirus Expression System", Biotechnol. Prog., 8, (1992), 391-396.

Zavodzky, P, et al., "Production of multidomain complement glycoproteins in insect cells", Cytotechnology, 20, (1996), 279-288.

Zhang, Fengrui, "The *Trichoplusia ni* cell line MSU-TnT4 does not harbor a latent nodavirus", In Vitro Cell.Dev.Biol.\_Animal, (2010), 1-6.

Zhao, Y, et al., "Expression of a Recombinant Bacilovirus for Vitronectin in Insect Cells—Purification, Characterization of Post-translational Modifications and Functional-Studies of the Recombinant Protein", Arch. Biochem. Biophys., 304, (1993), 434-442.

\* cited by examiner

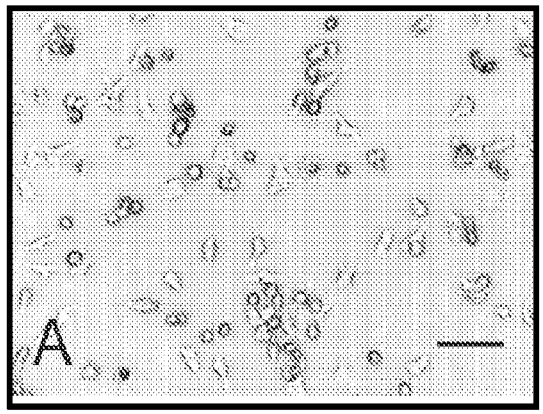 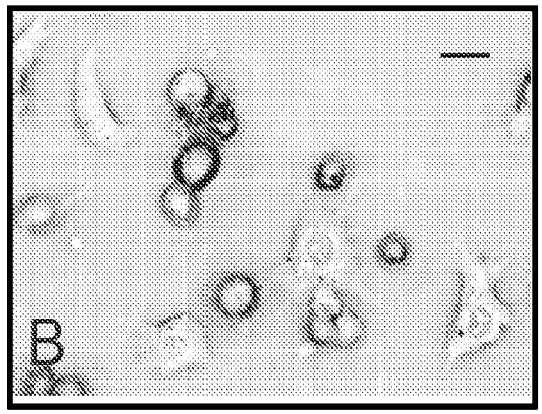
FIG. 2A　　　　　　　　FIG. 2B
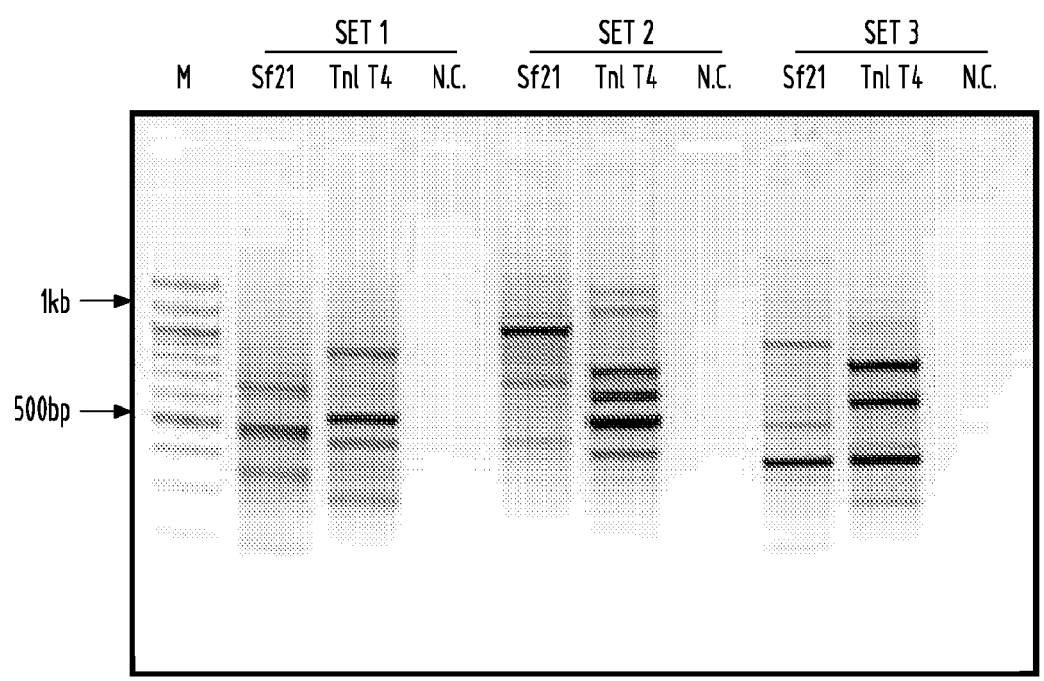
FIG. 3

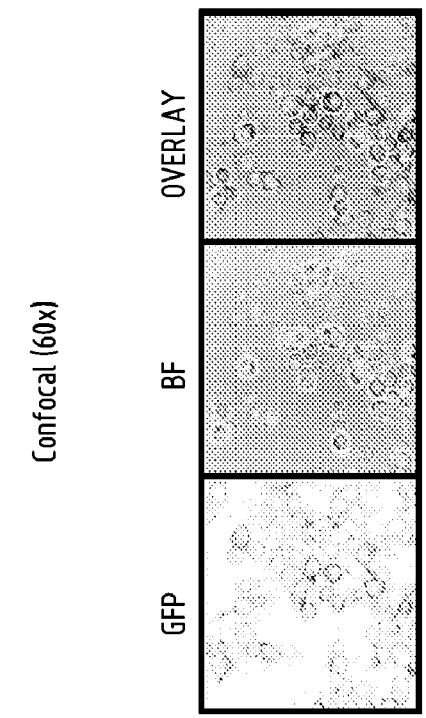
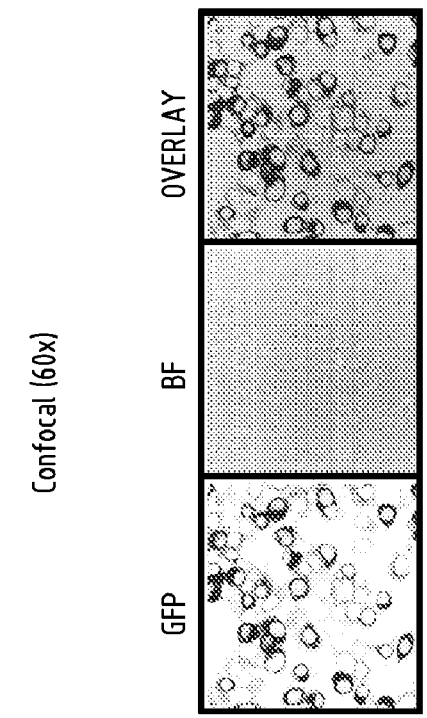
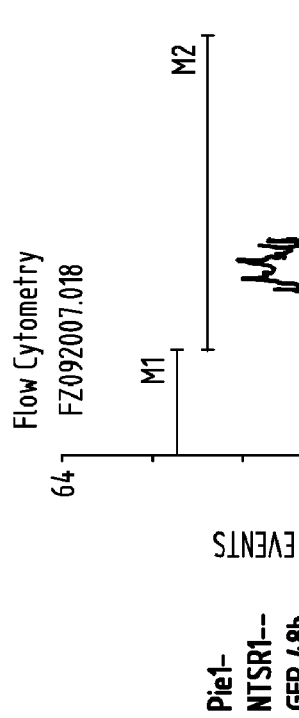
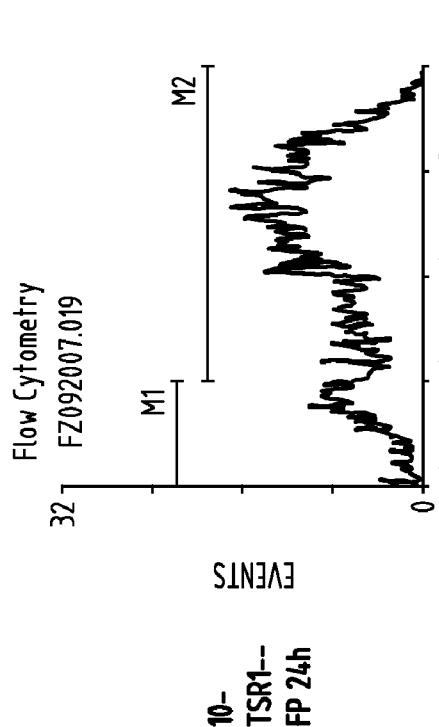
FIG. 6C
FIG. 6D

SEQUENCE LISTING

```
<160> NUMBER OF SEQ ID NOS: 23

<210> SEQ ID NO 1
<211> LENGTH: 4158
<212> TYPE: DNA
<213> ORGANISM: Homo sapiens

<400> SEQUENCE: 1
caagctcgcc   ccgcgcagcc   cgagccgggc   tgggcgctgt   cctcggggc    ctggggaacc       60 gcgcggtttg   gagatcggag   gcacctggaa   cccgtggcaa   gcgccgagcc   gggagacagc      120
ccgaggaacc   acgggttctg   gagctaggag   ccggaagctg   ggagtccgga   ggagagcgga      180
gcccggagcc   cggagcccgg   ggcggcgcgt   ctgggtctgg   cgcttcccga   ctggacggcg      240
cgcccgctgg   tcttcgccac   gcgccctccc   ctgggctccc   gttcatcggt   ccccgcctga      300
gacgcgccca   ctcctgcccg   gacttccagc   cccggaggcg   ccggacagag   ccgcggactc      360
cagcgcccac   catgcgcctc   aacagctccg   cgccgggaac   cccgggcacg   ccggccgccg      420
accccttcca   gcgggcgcag   gccggactgg   aggaggcgct   gctggccccg   ggcttcggca      480
acgcttcggg   caacgcgtcg   gagcgcgtcc   tggcggcacc   cagcagcgag   ctggacgtga      540
acaccgacat   ctactccaag   gtgctggtga   ccgccgtgta   cctggcgctc   ttcgtggtgg      600
gcacggtggg   caacacggtg   acggcgttca   cgctggcgcg   gaagaagtcg   ctgcagagcc      660
tgcagagcac   ggtgcattac   cacctgggca   gcctggcgct   gtccgacctg   ctcacctgc       720 tgctggccat   gcccgtggag   ctgtacaact   tcatctgggt   gcaccacccc   tgggccttcg      780
gcgacgccgg   ctgccgcgc   tactacttcc   tgcgcgacgc   ctgcacctac   gccacggccc       840
tcaacgtggc   cagcctgagt   gtggagcgct   acctggccat   ctgccaccc   ttcaaggcca       900
```

```
agaccctcat gtcccgaagc cgcaccaaga agttcatcag cgccatctgg ctcgcctcgg      960
ccctgctggc ggtgcctatg ctgttcacca tgggcgagca gaaccgcagc gccgacggcc     1020
agcacgccgg cggcctggtg tgcacccca ccatccacac tgccaccgtc aaggtcgtca      1080
tacaggtcaa caccttcatg tccttcatat tccccatggt ggtcatctcg gtcctgaaca     1140
ccatcatcgc caacaagctg accgtcatgg tacgccaggc ggccgagcag ggccaagtgt     1200
gcacggtcgg gggcgagcac agcacattca gcatggccat cgagcctggc agggtccagg     1260
ccctgcggca cggcgtgcgc gtcctacgtg cagtggtcat cgcctttgtg gtctgctggc     1320
tgccctacca cgtgcggcgc ctcatgttct gctacatctc ggatgagcag tggactccgt     1380
tcctctatga cttctaccac tacttctaca tggtgaccaa cgcactcttc tacgtcagct     1440
ccaccatcaa ccccatcctg tacaacctcg tctctgccaa cttccgccac atcttcctgg     1500
ccacactggc ctgcctctgc ccggtgtggc ggcgcaggag gaagaggcca gccttctcga     1560
ggaaggccga cagcgtgtcc agcaaccaca ccctctccag caatgccacc cgcgagacgc     1620
tgtactaggc tgtgcgcccc ggaacgtgtc caggaggagc ctggccatgg gtccttgccc     1680
ccgacagaca gagcagcccc cacccgggag ccttgatggg ggtcaggcag aggccagcct     1740
gcactggagt ctgaggcctg ggacccccc ctcccacccc ctaacccatg tttctcatta     1800
gtgtctcccg ggcctgtccc caactcctcc ccaccctcc cccatctcct ctttgaaagc      1860
cagaacaaga gagcgctcct ctcccagata ggaaaagggc ctctaacaag gagaaattag     1920
tgtgcggcaa aaggcagttt tctttgttct cagactaatg gatggttcca gagaaggaaa     1980
tgaaaggtgc tgggtggggc cgggcctccg gcggcccggc tgctgttccc atgtccacat     2040
ctctgaggcc tgcacccct ctgtctagct cggggagtcc agcccagtc ccgcaggctc       2100 cgtggctttg ggcctcacgt gcagaccctg ccatgcagac ccatgccccc ctcccccagg     2160
cagctccaag aaagctccct gactcgcccc ttcaggcctg gcaagctggg ggcccatcgc     2220
cgtggggagt ccctcccacc accctcgccg caggcagctg cagcccccag aggggaccac     2280
aagcccaaaa aggacaaaaa tgggctggcc tggaatggcc cagaccccag cctcccctcc     2340
tccctcccat cctcacccag gccaaggccc aggggtctg ccaggacacc acatgggagg      2400
gggctcaggc ctcagcctca agatcttcag ctgtggcctc tcgggctcgg cagaagggac     2460
gccggatcag gggcctggtc tccagcacct gcccgagtgg ccgtggccag gatgggtgc      2520 gcattccgtg tgctttgctt gtggctgtgc aggctgaggt ctggagccag gcccagagct     2580
ggcttcaggg tggggccttg agaagggaa tgtgggacag gggcgatggt gcctggtctc      2640
tgagtaagat gccaggtccc aggaactcag gcttcaggtg agaaggagcg gtgtgtccag     2700
gcaccgctgg ccggcagccc tgggctgagg cacagactca tttgtcacct tctggcggcg     2760
gcagccctgg ccccggcctc caagcagttg aaaaagctgg cgcctccttg gtctctagga     2820
tccaggctcc acagagcaca tgactagcca ggccctggc ttaagaaggt cgcctaagcc      2880
taagagaaga cagtcccagg agaagctggc cgggaccagc caggagctgg gagccacagg     2940
aagcaaaagt cagccttttc ttcaagggat ttccctgtct cagagcagcc tttgccccag     3000
ggaaatgggc tctgggctgg ctgcctgcac cggccatgtc gacccaggac ccggacacct     3060
ggtcttgggc tgtgttcagc cactttgcct tctctggact cagtttcccc gtctgagaaa     3120
tgagagtcga atgctacagt atctgcagtc gcttggatct ggctgttgag ttgacgggtt     3180
ccttgaaccc cacaaaatcc ctctccaacc acaggaccct tcggctcacc aagaacaggg     3240
cccaggggag tcaggcctat tcgctgcact tcctgccaaa ctttgccccc acaagcctgg     3300
```

-continued

```
tcatcagcca ggcagccctc ccagtgccca agggccacca accccaggga aacagggcca      3360
gcacagaggg gccttcctcc cccacagagc ccccatgaca tagtctgctc tgggcggaag      3420
agctttgctg ccagccaggg atgtccagag gtcagtgcag cccctacccc tgctcaggag      3480
tgggctcaga gtctagcaaa tgctaaggcc cctcaggctg ggctctgaac gaggacctgg      3540
actcagagcc agacagggca gcctcagacc cttctctggg gctcctggac cttgggccat      3600
aatttctgag cctcggtttc cccatctaag gaacagatgt ggtcgttccg ccctctcagc      3660
tggatgagac tgtcctggag gatccacccc ggaacagaca gaatggtgtc tctcaggatg      3720
gtgctctgag agagggcaga gtggatgccc cactgcccta gaccctcggt agacgtgggg      3780 tctctgggc ggggtctgtg gctgtgactg aagtcggctt ttcccgttga tgtcttgatg       3840
ctcctatctg tgcacttacc gtaggtaggg acacgtgtcc acgcaccaca gacacaccca      3900
cgacacctga tctcgtatca ctagcttgcg gccaggtcat gatgtggccc cggaagctgg      3960
ccctgcgtgc catgagtgcg tcggtcatgg agtccggagc ccctgagccg gcccctggtg      4020
acggcacagc cctcacagct caaacgccca ccccactcc caccatctgc aggtggtgaa      4080
aacaaacccc gtgtatctct caataaaggt ggccgaaggg cctcgatgtg gaaaaaaaaa      4140
aaaaaaaaaa aaaaaaaa                                                    4158

<210> SEQ ID NO 2
<211> LENGTH: 44
<212> TYPE: DNA
<213> ORGANISM: Artificial Sequence
<220> FEATURE:
<223> OTHER INFORMATION: Primer

<400> SEQUENCE: 2
atgcactagt aaagaattca ccatgcgcct caacagctcc gcgc                         44

<210> SEQ ID NO 3
<211> LENGTH: 39
<212> TYPE: DNA
<213> ORGANISM: Artificial Sequence
<220> FEATURE:
<223> OTHER INFORMATION: Primer

<400> SEQUENCE: 3
ggtaaagctt aaaccggtag cgtctcgcgg gtggcattg                               39

<210> SEQ ID NO 4
<211> LENGTH: 34
<212> TYPE: DNA
<213> ORGANISM: Artificial Sequence
<220> FEATURE:
<223> OTHER INFORMATION: Primer

<400> SEQUENCE: 4
tccaccggtc gccaccatgg tgagcaaggg cgag                                    34

<210> SEQ ID NO 5
<211> LENGTH: 36
<212> TYPE: DNA
<213> ORGANISM: Artificial Sequence
<220> FEATURE:
<223> OTHER INFORMATION: Primer

<400> SEQUENCE: 5
gataaagctt ataagatcta tattacttgt acagct                                  36

<210> SEQ ID NO 6
```

-continued

```
<211> LENGTH: 29
<212> TYPE: DNA
<213> ORGANISM: Artificial Sequence
<220> FEATURE:
<223> OTHER INFORMATION: Primer

<400> SEQUENCE: 6
gttggagtct agagtgctat tttacaaag                                    29

<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
gattggaatt caaatgtaat ttacagtata g                                 31

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
aagcttctag aatccgctca ccaaacg                                      27

<210> SEQ ID NO 9
<211> LENGTH: 26
<212> TYPE: DNA
<213> ORGANISM: Artificial Sequence
<220> FEATURE:
<223> OTHER INFORMATION: Primer

<400> SEQUENCE: 9
tttgcgtcat agtgaattcg ttgttc                                       26

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
ccgtcctcct tgaagtcgat gcc                                          23

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
acggtgcatt accacctggg cagcc                                        25

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
```

```
accatcatcg ccaacaagct gaccgtcatg                                      30
```

```
<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
caggaggaag aggccagcct tctcg                                           25
```

```
<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
acatccagat ccgatcaagt                                                 20
```

```
<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gccaggaatg ttgcttgcaa                                                 20
```

```
<210> SEQ ID NO 16
<211> LENGTH: 1257
<212> TYPE: DNA
<213> ORGANISM: Homo sapiens

<400> SEQUENCE: 16
atgcgcctca acagctccgc gccgggaacc ccgggcacgc cggccgccga cccttccag       60
cgggcgcagg ccggactgga ggaggcgctg ctggccccgg gcttcggcaa cgcttcgggc     120
aacgcgtcgg agcgcgtcct ggcggcaccc agcagcgagc tggacgtgaa caccgacatc     180
tactccaagg tgctggtgac cgccgtgtac ctggcgctct tcgtggtggg cacggtgggc     240
aacacggtga cggcgttcac gctggcgcgg aagaagtcgc tgcagagcct gcagagcacg     300
gtgcattacc acctgggcag cctggcgctg tccgacctgc tcaccctgct gctggccatg     360
cccgtggagc tgtacaactt catctgggtg caccacccct gggccttcgg cgacgccggc     420
tgccgcggct actacttcct gcgcgacgcc tgcacctacg ccacggccct caacgtggcc     480
agcctgagtg tggagcgcta cctggccatc tgccaccccc tcaaggccaa gaccctcatg     540
tcccgaagcc gcaccaagaa gttcatcagc gccatctggc tcgcctcggc cctgctggcg     600
gtgcctatgc tgttcaccat gggcgagcag aaccgcagcg ccgacggcca gcacgccggc     660
ggcctggtgt gcacccccac catccacact gccaccgtca aggtcgtcat acaggtcaac     720
accttcatgt ccttcatatt ccccatggtg gtcatctcgg tcctgaacac catcatcgcc     780
aacaagctga ccgtcatggt acgccaggcg gccgagcagg gccaagtgtg cacggtcggg     840
ggcgagcaca gcacattcag catggccatc gagcctggca gggtccaggc cctgcggcac     900
ggcgtgcgcg tctacgtgc agtggtcatc gcctttgtgg tctgctggct gccctaccac     960
gtgcggcgcc tcatgttctg ctacatctcg gatgagcagt ggactccgtt cctctatgac    1020
```

```
ttctaccact acttctacat ggtgaccaac gcactcttct acgtcagctc caccatcaac     1080
cccatcctgt acaacctcgt ctctgccaac ttccgccaca tcttcctggc cacactggcc     1140
tgcctctgcc cggtgtggcg gcgcaggagg aagaggccag ccttctcgag gaaggccgac     1200
agcgtgtcca gcaaccacac cctctccagc aatgccaccc gcgagacgct gtactag       1257
```

<210> SEQ ID NO 17
<211> LENGTH: 1789
<212> TYPE: DNA
<213> ORGANISM: Homo sapiens

<400> SEQUENCE: 17

```
caggtcctgg gagaggacag aaaacaactg ggactcctca gccccggca gctcccagtg      60 cccagccacc cacaacacaa cccaaagcct tctagacaag ctcagtggaa tctgaagggc    120
ccaccccatg gaggaatgct gggtgacaga gatagccaat ggctccaagg atggcttgga    180
ttccaaccct atgaaggatt acatgatcct gagtggtccc cagaagacag ctgttgctgt    240
gttgtgcact cttctgggcc tgctaagtgc cctggagaac gtggctgtgc tctatctgat    300
cctgtcctcc caccaactcc gccggaagcc ctcatacctg ttcattggca gcttggctgg    360
ggctgacttc ctggccagtg tggtcttttgc atgcagcttt gtgaatttcc atgttttcca    420
tggtgtggat tccaaggctg tcttcctgct gaagattggc agcgtgacta tgaccttcac    480
agcctctgtg ggtagcctcc tgctgaccgc cattgaccga tacctctgcc tgcgctatcc    540
accttcctac aaagctctgc tcacccgtgg aagggcactg gtgaccctgg gcatcatgtg    600
ggtcctctca gcactagtct cctacctgcc cctcatggga tggacttgct gtcccaggcc    660
ctgctctgag cttttcccac tgatccccaa tgactacctg ctgagctggc tcctgttcat    720
cgccttcctc ttttccggaa tcatctacac ctatgggcat gttctctgga aggcccatca    780
gcatgtggcc agcttgtctg gccaccagga caggcaggtg ccaggaatgg cccgaatgag    840
gctggatgtg aggttggcca agaccctagg gctagtgttg gctgtgctcc tcatctgttg    900
gttcccagtg ctggccctca tggcccacag cctggccact acgctcagtg accaggtcaa    960
gaaggccttt gctttctgct ccatgctgtg cctcatcaac tccatggtca accctgtcat    1020
ctatgctcta cggagtggag agatccgctc ctctgcccat cactgcctgg ctcactggaa    1080
gaagtgtgtg aggggccttg ggtcagaggc aaaagaagaa gccccgagat cctcagtcac    1140
cgagacagag gctgatggga aaatcactcc gtggccagat ccagagatc tagacctctc     1200 tgattgctga tgaggcctct tcccaattta acaactcaa gtcagaaatc agttcactcc     1260
ctggaagaga gagggggtc ttggcactct cttcttactt aaaccagtcc cagacaccta    1320
gacacggacc ccttttgct gatgagtgtt gggactgact cctggaagac agcctggcct    1380
tgcccacctg cacacagtct gttggatagg tagggccacg aggagtagcc aggtaggcga    1440
gacacaaaag gcctgggaca gggtcagtac aagtcaggtc aggcttcatg cctgcatcct    1500
ccagagacca caggagccaa agcgagcctc caggcccagc aatgagggac ttgggagaaa    1560
tctgagaaga atgggttgtt ctcttgggaa gtcagggtat cagatgggat ggacatccag    1620
gtcttctctc tgcctaattg tcaaggcctc cttggctctg gagctatgaa aggccccact    1680
ttcaagtcac ccttgccact gaggaccgag gactatgcta tgatgaggat taaggtgttg    1740
acttgcctct ttcagagata aatgacaagc cttcaaaaaa aaaaaaaa                 1789
```

<210> SEQ ID NO 18
<211> LENGTH: 1083
<212> TYPE: DNA

-continued

<213> ORGANISM: Homo sapiens

<400> SEQUENCE: 18

```
atggaggaat gctgggtgac agagatagcc aatggctcca aggatggctt ggattccaac      60
cctatgaagg attacatgat cctgagtggt ccccagaaga cagctgttgc tgtgttgtgc     120
actcttctgg gcctgctaag tgccctggag aacgtggctg tgctctatct gatcctgtcc     180
tcccaccaac tccgccggaa gccctcatac ctgttcattg gcagcttggc tggggctgac     240
ttcctggcca gtgtggtctt tgcatgcagc tttgtgaatt ccatgttttt ccatggtgtg     300
gattccaagg ctgtcttcct gctgaagatt ggcagcgtga ctatgacctt cacagcctct     360
gtgggtagcc tcctgctgac cgccattgac cgatacctct gcctgcgcta ccaccttcc      420
tacaaagctc tgctcacccg tggaagggca ctggtgaccc tgggcatcat gtgggtcctc     480
tcagcactag tctcctacct gcccctcatg ggatggactt gctgtcccag gccctgctct     540
gagcttttcc cactgatccc caatgactac ctgctgagct ggctcctgtt catcgccttc     600
ctctttccg gaatcatcta cacctatggg catgttctct ggaaggccca tcagcatgtg     660
gccagcttgt ctggccacca ggacaggcag gtgccaggaa tgcccgaat gaggctggat     720
gtgaggttgg ccaagaccct agggctagtg ttggctgtgc tcctcatctg ttggttccca     780
gtgctggccc tcatgcccca cagcctggcc actacgctca gtgaccaggt caagaaggcc     840
tttgctttct gctccatgct gtgcctcatc aactccatgg tcaaccctgt catctatgct     900
ctacggagtg gagagatccg ctcctctgcc catcactgcc tggctcactg aagaagtgt      960
gtgaggggcc ttgggtcaga ggcaaaagaa gaagccccga gatcctcagt caccgagaca    1020
gaggctgatg ggaaaatcac tccgtggcca gattccagag atctagacct ctctgattgc    1080
tga                                                                  1083
```

<210> SEQ ID NO 19
<211> LENGTH: 2492
<212> TYPE: DNA
<213> ORGANISM: Homo sapiens

<400> SEQUENCE: 19

```
agaaacagga gcagatgtac agggtttgcc tgactcacac tcaaggttgc ataagcaaga      60
tttcaaaatt aatcctattc tggagacctc aacccaatgt acaatgttcc tgactggaaa     120
agaagaacta tattttttctg atttttttttt tcaaatcttt accattagtt gccctgtatc     180
tccgccttca ctttctgcag gaaactttat ttcctacttc tgcatgccaa gtttctacct     240
ctagatctgt ttggttcagt tgctgagaag cctgacatac caggactgcc tgagacaagc     300
cacaagctga acagagaaag tggattgaac aaggacgcat tccccagta catccacaac      360
atgctgtcca catctcgttc tcggtttatc agaaatacca acgagagcgg tgaagaagtc     420
accaccttttt ttgattatga ttacggtgct ccctgtcata aatttgacgt gaagcaaatt     480
ggggcccaac tcctgcctcc gctctactcg ctggtgttca tctttggttt tgtgggcaac     540
atgctggtcg tcctcatctt aataaactgc aaaaagctga agtgcttgac tgacatttac     600
ctgctcaacc tggccatctc tgatctgctt tttcttatta ctctcccatt gtgggctcac     660
tctgctgcaa atgagtgggt ctttgggaat gcaatgtgca attattcac agggctgtat     720
cacatcggtt attttggcgg aatcttcttc atcatcctcc tgacaatcga tagataccttg     780
gctattgtcc atgctgtgtt tgcttttaaaa gccaggacgg tcacctttgg ggtggtgaca    840
agtgtgatca cctggttggt ggctgtgttt gcttctgtcc caggaatcat ctttactaaa    900
```

| | | |
|---|---|---|
| tgccagaaag aagattctgt ttatgtctgt ggcccttatt ttccacgagg atggaataat | 960 | |
| ttccacacaa taatgaggaa cattttgggg ctggtcctgc cgctgctcat catggtcatc | 1020 | |
| tgctactcgg gaatcctgaa aaccctgctt cggtgtcgaa acgagaagaa gaggcatagg | 1080 | |
| gcagtgagag tcatcttcac catcatgatt gtttactttc tcttctggac tccctataat | 1140 | |
| attgtcattc tcctgaacac cttccaggaa ttcttcggcc tgagtaactg tgaaagcacc | 1200 | |
| agtcaactgg accaagccac gcaggtgaca gagactcttg gatgactca ctgctgcatc | 1260 | |
| aatcccatca tctatgcctt cgttggggag aagttcagaa ggtatctctc ggtgttcttc | 1320 | |
| cgaaagcaca tcaccaagcg cttctgcaaa caatgtccag ttttctacag ggagacagtg | 1380 | |
| gatggagtga cttcaacaaa cacgccttcc actggggagc aggaagtctc ggctggttta | 1440 | |
| taaaacgagg agcagtttga ttgttgttta aaagggaga taacaatctg tatataacaa | 1500 | |
| caaacttcaa gggtttgttg aacaatagaa acctgtaaag caggtgccca ggaacctcag | 1560 | |
| ggctgtgtgt actaatacag actatgtcac ccaatgcata tccaacatgt gctcagggaa | 1620 | |
| taatccagaa aaactgtggg tagagacttt gactctccag aaagctcatc tcagctcctg | 1680 | |
| aaaaatgcct cattaccttg tgctaatcct cttttctag tcttcataat ttcttcactc | 1740 | |
| aatctctgat tctgtcaatg tcttgaaatc aagggccagc tggaggtgaa gaagagaatg | 1800 | |
| tgacaggcac agatgaatgg gagtgaggga tagtggggtc agggctgaga ggagaaggag | 1860 | |
| ggagacatga gcatggctga gcctggacaa agacaaaggt gagcaaaggg ctcacgcatt | 1920 | |
| cagccaggag atgatactgg tccttagccc catctgccac gtgtatttaa ccttgaaggg | 1980 | |
| ttcaccaggt cagggagagt ttgggaactg caataacctg ggagttttgg tggagtccga | 2040 | |
| tgattctctt ttgcataagt gcatgacata ttttgctttt attacagttt atctatggca | 2100 | |
| cccatgcacc ttacatttga aatctatgaa atatcatgct ccattgttca gatgcttctt | 2160 | |
| aggccacatc cccctgtcta aaaattcaga aaattttgt ttataaaga tgcattatct | 2220 | |
| atgatatgct aatatatgta tatgcaatat atataggctc ttgcttgatc tctccaggag | 2280 | |
| gtagtgatta tgagaagggg gtggagaatg atgagttcct tcaccaggag caaaggacgg | 2340 | |
| ggatcgtgtg gaaccactgc agaactattt ccgaaatcaa ctaagtggag agagccagga | 2400 | |
| aggctgcatc agaacccagt aaagcttctt gtctggatct gagctggttt gttttgtgct | 2460 | |
| tgcttttccc tgccttgcca ctcccctcac tc | 2492 | |

<210> SEQ ID NO 20
<211> LENGTH: 1083
<212> TYPE: DNA
<213> ORGANISM: Homo sapiens

<400> SEQUENCE: 20

| | | |
|---|---|---|
| atgctgtcca catctcgttc tcggtttatc agaaatacca acgagagcgg tgaagaagtc | 60 | |
| accacctttt ttgattatga ttacggtgct ccctgtcata aatttgacgt gaagcaaatt | 120 | |
| ggggcccaac tcctgcctcc gctctactcg ctggtgttca tctttggttt tgtgggcaac | 180 | |
| atgctggtcg tcctcatctt aataaactgc aaaaagctga agtgcttgac tgacatttac | 240 | |
| ctgctcaacc tggccatctc tgatctgctt tttcttatta ctctcccatt gtgggctcac | 300 | |
| tctgctgcaa atgagtgggt cttgggaat gcaatgtgca attattcac agggctgtat | 360 | |
| cacatcggtt attttggcgg aatcttcttc atcatcctcc tgacaatcga tagatacctg | 420 | |
| gctattgtcc atgctgtgtt tgcttttaaaa gccaggacgg tcacctttgg ggtggtgaca | 480 | |
| agtgtgatca cctggttggt ggctgtgttt gcttctgtcc caggaatcat ctttactaaa | 540 | |

-continued

| | |
|---|---|
| tgccagaaag aagattctgt ttatgtctgt ggcccttatt ttccacgagg atggaataat | 600 |
| ttccacacaa taatgaggaa catttttgggg ctggtcctgc cgctgctcat catggtcatc | 660 |
| tgctactcgg gaatcctgaa aaccctgctt cggtgtcgaa acgagaagaa gaggcatagg | 720 |
| gcagtgagag tcatcttcac catcatgatt gtttactttc tcttctggac tccctataat | 780 |
| attgtcattc tcctgaacac cttccaggaa ttcttcggcc tgagtaactg tgaaagcacc | 840 |
| agtcaactgg accaagccac gcaggtgaca gagactcttg gatgactca ctgctgcatc | 900 |
| aatcccatca tctatgcctt cgttggggag aagttcagaa ggtatctctc ggtgttcttc | 960 |
| cgaaagcaca tcaccaagcg cttctgcaaa caatgtccag ttttctacag ggagacagtg | 1020 |
| gatggagtga cttcaacaaa cacgccttcc actggggagc aggaagtctc ggctggttta | 1080 |
| taa | 1083 |

<210> SEQ ID NO 21
<211> LENGTH: 2452
<212> TYPE: DNA
<213> ORGANISM: Mus musculus

<400> SEQUENCE: 21

| | |
|---|---|
| gccggcggcc agggcgagcg cttactggca acacgatgcg gtccttgctg ctgttcactt | 60 |
| tctcggcgtg cgtgctgctg gcccgggtgc tgctggctgg cggcgcgagc agcggcgccg | 120 |
| gggacacccg gccaggcagc aggcgccggg cgagagaggc gctggcggct caaaagatcg | 180 |
| aggtgcttgt tctattgccc cggagacgatt cgtacttgtt ctcgctggcc cgggtgaggc | 240 |
| cggccatcga gtacgcgctg cgtagcgtgg agggcaatgg caccgggagg aagctgctgc | 300 |
| cgccgggcac tcgcttccag gtggcctacg aagactcgga ctgcggcaac cgcgcgctct | 360 |
| tcagtcttgt ggaccgcgtg gcggcggcgc gcggcgccaa gccggatctc atcctggggc | 420 |
| ccgtgtgcga gtacgcggcg cgccggtgg ctcggctggc gtctcactgg gacctgccga | 480 |
| tgctgtccgc aggagcgctg gccgccggtt ccagcacaa ggacacggaa tactcgcacc | 540 |
| tcacgcgcgt ggcgcctgcc tacgccaaga tgggagagat gatgctcgct ctgtttcgcc | 600 |
| accaccactg gagccgtgca gccctggtct acagcgacga caaactcgag aggaactgtt | 660 |
| atttcacccct cgaggggtc cacgaggttt ttcaggagga ggggttgcac acgtctgcct | 720 |
| acaatttcga cgaaaccaaa gacttggacc tggacgacat agtgcgctac atccaaggca | 780 |
| gcgagcgagt ggtgatcatg tgtgccagtg gtgacaccat tcggagaatc atgttggcgg | 840 |
| tgcacagaca cggcatgacc agtggagact acgctttctt caacattgaa ctcttcaaca | 900 |
| gttcttccta cggagatggc tcgtggagga gggagacaa acacgactct gaagctaaac | 960 |
| aagcatactc gtccctccaa acagtcactc tactgaggac cgtgaaacct gagtttgaga | 1020 |
| agttttccat ggaggtgaaa agttctgttg agaaacaagg gctcaatgag gaggattacg | 1080 |
| tgaacatgtt tgttgaaggg ttccatgacg ccatcctcct ctacgttctg ctttacacg | 1140 |
| aagtgctcag agctggctac agcaagaagg atgggggaa aatcatccag cagacttgga | 1200 |
| acaggacatt tgaaggtatc gctggcagg tgtccataga tgccaacggg accggtatg | 1260 |
| gggacttctc tgtggttgcc atgactgaca ctgaagcagg cacccaagag gtcattggtg | 1320 |
| attactttgg gaagaaggc cggttccaaa tgcgatcgaa tgtcaaatat ccttggggcc | 1380 |
| ctttgaaact gagactagat gagaccagaa tcgtggagca taccaacagc tctccttgca | 1440 |
| aatcatgtgg cctagaagaa tctgcagtga caggaatcgt tgtgggggcc ctactaggtg | 1500 |
| ctggcttgct aatggccttc tacttttca ggaagaaata cagaataacc attgagaggc | 1560 |

-continued

| | |
|---|---|
| gaaatcagca agaggaaagc aacatcggga agcatcgaga gctgcgggaa gattccatca | 1620 |
| gatcacattt ttcggtggct taaaagagat gccctctcg cttcgtctac ttgagattcc | 1680 |
| ttaaagagat agatggaagg acagacatca acggagcaga aagggcgttc tcggagaagt | 1740 |
| cattcttta agcagtagtc atttcatttt acattttctt tagaagctca ggaatgattg | 1800 |
| ttaatcacta tctgccttct ggcctctcat ctcatggcaa actaatataa tgaaacaacg | 1860 |
| caatgctgtt aagtgttctg gctgctggag gggcatcaga ggagatttat gtcttgaaag | 1920 |
| tctgctgcat ccatatcttg attgctttgg gggcagttca cacgaggata gaaaaatgtg | 1980 |
| gcttttctga aatgaaatgt tttgtagcta ggataaaaca attttttacaa ggagaatatt | 2040 |
| cttggaaaga atttaacacc caataagagg acaatggaat gaaagaaatc tccaggctgg | 2100 |
| gaatgcagtg ccctctctc tggaactggg ggacaggttt tgggttgatg aaggctgcgt | 2160 |
| ccaacgtcca cattcaggtc tgaattcata tctcaagaaa ggatcctccc tgtctctttt | 2220 |
| agtgtctcat cagagctact ctggaaaact gtaaatatta gtgagcaagg aggatttata | 2280 |
| taagaaaatt gagtctaaaa tgcttcttat acgatgtaaa aaagtcccta cttcacacta | 2340 |
| acattttatt tttaagtatt ttaatcttat attttggtat tagaaatgtg tctatttttt | 2400 |
| cattttgaag attaaattc acttatattt taagagcaaa aaaaaaaaa aa | 2452 |

<210> SEQ ID NO 22
<211> LENGTH: 1608
<212> TYPE: DNA
<213> ORGANISM: Mus musculus

<400> SEQUENCE: 22

| | |
|---|---|
| atgcggtcct tgctgctgtt cactttctcg gcgtgcgtgc tgctggcccg ggtgctgctg | 60 |
| gctggcggcg cgagcagcgg cgccggggac acccggccag cagcaggcg ccgggcgaga | 120 |
| gaggcgctgg cggctcaaaa gatcgaggtg cttgttctat tgccccggga cgattcgtac | 180 |
| ttgttctcgc tggcccgggt gaggccgcc atcgagtacg cgctgcgtag cgtggagggc | 240 |
| aatggcaccg ggaggaagct gctgccgccg ggcactcgct tccaggtggc ctacgaagac | 300 |
| tcggactgcg gcaaccgcgc gctcttcagt cttgtggacc gcgtggcggc ggcgcgcggc | 360 |
| gccaagccgg atctcatcct ggggcccgtg tgcgagtacg cggcggcgcc ggtggctcgg | 420 |
| ctggcgtctc actgggacct gccgatgctg tccgcaggag cgctggccgc cggtttccag | 480 |
| cacaaggaca cggaatactc gcacctcacg cgcgtggcgc ctgcctacgc aagatgggga | 540 |
| gagatgatgc tcgctctgtt tcgccaccac cactggagcc gtgcagccct ggtctacagc | 600 |
| gacgacaaac tcgagaggaa ctgttatttc accctcgagg gggtccacga ggttttttcag | 660 |
| gaggaggggt gcacacgtc tgcctacaat ttcgacgaaa ccaaagactt ggacctggac | 720 |
| gacatagtgc gctacatcca aggcagcgag cgagtggtga tcatgtgtgc cagtggtgac | 780 |
| accattcgga gaatcatgtt ggcggtgcac agacacggca tgaccagtgg agactacgct | 840 |
| tccttcaaca ttgaactctt caacagttct tcctacgag atggctcgtg gaggagagga | 900 |
| gacaaacacg actctgaagc taaacaagca tactcgtccc tccaaacagt cactctactg | 960 |
| aggaccgtga aacctgagtt tgagaagttt tccatggagg tgaaaagttc tgttgagaaa | 1020 |
| caagggctca atgaggagga ttacgtgaac atgtttgttg aagggttcca tgacgccatc | 1080 |
| ctcctctacg ttctggcttt acacgaagtg ctcagagctg gctacagcaa gaaggatggg | 1140 |
| gggaaaatca tccagcagac ttggaacagg acatttgaag gtatcgctgg gcaggtgtcc | 1200 |
| atagatgcca acggggaccg gtatggggac ttctctgtgg ttgccatgac tgacactgaa | 1260 |

-continued

| | |
|---|---|
| gcaggcaccc aagaggtcat tggtgattac tttgggaaag aaggccggtt ccaaatgcga | 1320 |
| tcgaatgtca aatatccttg gggccctttg aaactgagac tagatgagac cagaatcgtg | 1380 |
| gagcatacca acagctctcc ttgcaaatca tgtggcctag aagaatctgc agtgacagga | 1440 |
| atcgttgtgg gggccctact aggtgctggc ttgctaatgg ccttctactt tttcaggaag | 1500 |
| aaatacagaa taaccattga gaggcgaaat cagcaagagg aaagcaacat cgggaagcat | 1560 |
| cgagagctgc gggaagattc catcagatca catttttcgg tggcttaa | 1608 |

<210> SEQ ID NO 23
<211> LENGTH: 2616
<212> TYPE: DNA
<213> ORGANISM: Homo sapiens

<400> SEQUENCE: 23

| | |
|---|---|
| atggcggatt ccagcgaagg cccccgcgcg gggcccgggg aggtggctga gctccccggg | 60 |
| gatgagagtg gcaccccagg tggggaggct tttcctctct cctccctggc caatctgttt | 120 |
| gaggggagg atggctccct ttcgccctca ccggctgatg ccagtcgccc tgctggccca | 180 |
| ggcgatgggc gaccaaatct gcgcatgaag ttccagggcg ccttccgcaa ggggggtgccc | 240 |
| aaccccatcg atctgctgga gtccacccta tatgagtcct cggtggtgcc tgggcccaag | 300 |
| aaagcaccca tggactcact gtttgactac ggcacctatc gtcaccactc cagtgacaac | 360 |
| aagaggtgga ggaagaagat catagagaag cagccgcaga gccccaaagc ccctgcccct | 420 |
| cagccgcccc ccatcctcaa agtcttcaac cggcctatcc tctttgacat cgtgtcccgg | 480 |
| ggctccactg ctgacctgga cgggctgctc ccattcttgc tgacccacaa gaaacgccta | 540 |
| actgatgagg agtttcgaga gccatctacg gggaagacct gcctgcccaa ggccttgctg | 600 |
| aacctgagca atggccgcaa cgacaccatc cctgtgctgc tggacatcgc ggagcgcacc | 660 |
| ggcaacatgc gggagttcat taactcgccc ttccgtgaca tctactatcg aggtcagaca | 720 |
| gccctgcaca tcgccattga gcgtcgctgc aaacactacg tggaacttct cgtggcccag | 780 |
| ggagctgatg tccacgccca ggccgtgggg cgcttcttcc agcccaagga tgaggggggc | 840 |
| tacttctact ttggggagct gccccctgtcg ctggctgcct gcaccaacca gccccacatt | 900 |
| gtcaactacc tgacggagaa ccccccacaag aaggcggaca tgcggcgcca ggactcgcga | 960 |
| ggcaacacag tgctgcatgc gctggtggcc attgctgaca cacccgtgaa acaccaag | 1020 |
| tttgttacca agatgtacga cctgctgctg ctcaagtgtg cccgcctctt ccccgacagc | 1080 |
| aacctggagg ccgtgctcaa caacgacggc ctctcgcccc tcatgatggc tgccaagacg | 1140 |
| ggcaagattg ggatctttca gcacatcatc cggcgggagg tgacggatga ggacacacgg | 1200 |
| cacctgtccc gcaagttcaa ggactgggcc tatgggccag tgtattcctc gctttatgac | 1260 |
| ctctcctccc tggacacgtg tgggaagag gcctccgtgc tggagatcct ggtgtacaac | 1320 |
| agcaagattg agaaccgcca cgagatgctg ctgtgtgagc ccatcaatga actgctgcgg | 1380 |
| gacaagtggc gcaagttcgg ggccgtctcc ttctacatca acgtggtctc ctacctgtgt | 1440 |
| gccatggtca tcttcactct caccgcctac taccagccgc tggagggcac accgccgtac | 1500 |
| ccttaccgca ccacggtgga ctacctgcgg ctggctggcg aggtcattac gctcttcact | 1560 |
| ggggtccctgt tcttcttcac caacatcaaa gacttgttca tgaagaaatg ccctggagtg | 1620 |
| aattctctct tcattgatgg ctccttccag ctgctctact tcatctactc tgtcctggtg | 1680 |
| atcgtctcag cagccctcta cctggcaggg atcgaggcct acctggccgt gatggtcttt | 1740 |
| gccctggtcc tgggctggat gaatgccctt tacttcaccc gtgggctgaa gctgacgggg | 1800 |

-continued

```
acctatagca tcatgatcca gaagattctc ttcaaggacc ttttccgatt cctgctcgtc    1860
tacttgctct tcatgatcgg ctacgcttca gccctggtct ccctcctgaa cccgtgtgcc    1920
aacatgaagg tgtgcaatga ggaccagacc aactgcacag tgcccactta cccctcgtgc    1980
cgtgacagcg agaccttcag caccttcctc ctggacctgt ttaagctgac catcggcatg    2040
ggcgacctgg agatgctgag cagcaccaag taccccgtgg tcttcatcat cctgctggtg    2100
acctacatca tcctcacctt tgtgctgctc ctcaacatgc tcattgccct catgggcgag    2160
acagtgggcc aggtctccaa ggagagcaag cacatctgga agctgcagtg ggccaccacc    2220
atcctggaca ttgagcgctc cttccccgta ttcctgagga aggccttccg ctctggggag    2280
atggtcaccg tgggcaagag ctcggacggc actcctgacc gcaggtggtg cttcagggtg    2340
gatgaggtga actggtctca ctggaaccag aacttgggca tcatcaacga ggacccgggc    2400
aagaatgaga cctaccagta ttatggcttc tcgcataccg tgggccgcct ccgcagggat    2460
cgctggtcct cggtggtacc ccgcgtggtg gaactgaaca agaactcgaa cccggacgag    2520
gtggtggtgc ctctggacag catggggaac ccccgctgcg atggccacca gcagggttac    2580
ccccgcaagt ggaggactga ggacgccccg ctctag                              2616
```

TRICHOPLUSIA NI CELL LINE AND METHODS OF USE

CROSS-REFERENCE TO RELATED APPLICATIONS

This application is a National Stage of PCT/US2009/040554, filed Apr. 14, 2009, which claims priority to U.S. Provisional Patent Application No. 61/044,729 filed Apr. 14, 2008.

FIELD OF THE INVENTION

This invention is in the field of cell biology, medicine, and agriculture and, more specifically, relates to an isolated insect cell line and methods of using the cell line.

BACKGROUND OF THE INVENTION

The baculovirus expression vector system (BEVS) is one of the most widely used gene expression systems for eukaryotic proteins because the proteins are properly processed with protein modifications such as phosphorylation, acetylation, and glycosylation (Becker et al. 1994; Grunewald et al. 1996; Ng et al. 1993; Ng et al. 1994; Zavodzky and Cseh 1996; Zhao and Sane 1993). See also, Lucow, V. A. and Summers, M. D. "High level expression of non-fused foreign genes with *Autographa californica* nuclear polyhedrosis virus expression vectors, *Virology,* 170:311-39 (1988); and U.S. Pat. No. 4,745,051. The baculovirus *Autographa californica* multiple nucleopolyhedrovirus (AcMNPV) is the basis of the BEVS owing to its ability to express high levels of protein from its polyhedrin gene (polh) promoter. To express proteins, cultured insect cells are infected by recombinant AcMNPV, which carries the gene encoding the protein of interest.

Although the interest, need, and development of more insect cell lines has grown exponentially since the first insect cell lines were created by Gao (Gaw) and by Grace (Gaw et al. 1959; Grace 1962), currently there are only a few cell lines commercially available for use with the BEVS. These include "Sf21" derived from *Spodoptera frugiperda* (Vaughn et al. 1977) and BTI-Tn-5B1-4 ("Hi-5") cells derived from *Trichoplusia ni* (Granados et al. 1994; McKenna et al. 1998), along with a clonal isolate of Sf21 called Sf9 cells (Smith et al. 1985). A genetically engineered Sf9 cell line called "Mimic" is also available from Invitrogen. Mimic cells are engineered to express five mammalian genes encoding glycosyltransferases enabling the cells to synthesize complex mono-sialylated N-glycans typical of mammalian but not most insect cells (Hollister et al. 2002).

Whereas many proteins are expressed efficiently using one of these currently available cell lines, many other proteins are expressed poorly, if at all. The reasons some proteins are poorly expressed in BEVS is not understood. In some cases, a change in the cell line used results in improved expression (Akermoun et al. 2005; Chai et al. 1996; Ogonah et al. 1996; Palomares et al. 2003). Thus a broader selection of cell lines available for BEVS is needed, and would be expected to increase the versatility of this expression system.

Membrane proteins are a major class of protein that is difficult to express to high levels in any heterologous expression system, but have been expressed with some success using BEVS (Akermoun et al. 2005; Grisshammer and Tate 1995; Massotte 2003; McCusker et al. 2007; Sarramegna et al. 2003). Sequencing the human genome revealed that membrane proteins make up approximately 30% of all of the encoded proteins, yet the structures for less than 3% have been solved. Membrane proteins are crucial for transport and signal transduction across membranes and play important roles in many medical conditions such as cancer, hypertension, and mental illness, thus they are major and important targets for drug development. Knowledge of membrane protein structure and function is critical for understanding their roles in these conditions and for drug development. Membrane proteins also are key targets for insecticides. Understanding how the structures of potential insecticide targets differ from their vertebrate counterparts also would be invaluable for developing new and safer chemicals for use in agriculture.

Most membrane proteins are not sufficiently abundant in nature to purify and crystallize and no gene expression system has been able to reliably express membrane proteins in sufficient quantities for these studies. The BEVS is efficient at expressing both cytoplasmic and secreted proteins and has been used to successfully express some membrane proteins at high levels (Grisshammer and Tate 1995; Massotte 2003). However, despite some success, many membrane proteins cannot be expressed at high enough levels for structural and functional studies.

SUMMARY OF THE INVENTION

A new cell line, MSU-TnT4 ("TnT4"), was established from *Trichoplusia ni* embryos. More specifically, the present invention includes the TnT4 *Trichoplusia ni* cell line deposited with the American Type Culture Collection, 10801 University Blvd., Manassas, Va. 20110-2209, a recognized public depository for strains of microorganisms, under the provisions of the Budapest Treaty, as Patent Deposit Designation PTA-9384, having been deposited on Jul. 24, 2008. The cell line will be irrevocably available from the ATCC for the life of the patent. This cell line can be used with baculovirus expression vectors and for protein production e.g., membrane protein production.

To evaluate protein synthesis (e.g., membrane protein synthesis) in TnT4 cells, recombinant baculoviruses were constructed to express various proteins as enhanced green fluorescent protein (GFP) fusion proteins. The proteins expressed were human neurotensin receptor 1 (NTSR1), human cannabinoid receptor 2 (hCR2), cytokine receptor 2B (CCR2B), natriuretic peptide receptor C (NPR3), transient receptor potential vanilloid 4 (TRPV4) and secreted alkaline phosphatase (SEAP).

The nucleotide sequence for NTSR1 is identified in the Sequence Listing submitted herewith as SEQ ID NO: 1 and the coding region for NTSR1 (beginning with the start codon and ending with the stop codon) is identified in the Sequence Listing submitted herewith as SEQ ID NO: 16. The nucleotide sequence for hCR2 is identified in the Sequence Listing submitted herewith as SEQ ID NO: 17 and the coding region for hCR2 (beginning with the start codon and ending with the stop codon) is identified in the Sequence Listing submitted herewith as SEQ ID NO: 18, and has a Genbank Accession no. BC069722. The nucleotide sequence for CCR2B is identified in the Sequence Listing submitted herewith as SEQ ID NO: 19 and the coding region for CCR2B (beginning with the start codon and ending with the stop codon) is identified in the Sequence Listing submitted herewith as SEQ ID NO: 20, and has a Genbank Accession no. NM-000648. The nucleotide sequence for NPR3 is identified in the Sequence Listing submitted herewith as SEQ ID NO: 21 and the coding region for NPR3 (beginning with the start codon and ending with the stop codon) is identified in the Sequence Listing submitted herewith as SEQ ID NO: 22, and has a Genbank Accession no. BCO55897. The nucleotide sequence for the coding region of TRPV4 (beginning with the start codon and ending with the stop codon) is identified in the Sequence Listing submitted herewith as SEQ ID NO: 23, and has a GenBank Accession no. AF258465.

The present invention includes an isolated *Trichoplusia ni* cell wherein a sample of said cell has been deposited as ATCC Accession No. PTA-9384 ("TnT4"). The cell may be infected by a BEVS vector and this vector may carry a heterologous oligonucleotide that encodes a polypeptide. The oligonucleotide may be selected from the oligonucleotides having SEQ ID NOs. 1, and 16-23 or a substantially identical oligonucleotide; or the polypeptide may be a protein, such as a G-protein coupled receptor, or a fusion protein (e.g., the fusion protein may be a protein and a marker protein). The protein may be human neurotensin receptor 1 (NTSR1), human cannabinoid receptor 2 (hCR2), cytokine receptor 2B (CCR2B), natriuretic peptide receptor C (NPR3), transient receptor potential vanilloid 4 (TRPV4) and secreted alkaline phosphatase (SEAP), and conservative amino acid substitution variants thereof; and in the case of the fusion protein, the marker protein may be green fluorescent protein (GFP).

Also included is a method of producing a polypeptide including: providing an isolated cell from the TnT4 cell line which includes a heterologous oligonucleotide that encodes a polypeptide; growing the cell such that the polypeptide is expressed; and isolating the expressed polypeptide from the cell. The expressed polypeptide may be a protein, for example, a G-protein coupled receptor. The expressed polypeptide may be NTSR1, hCR2, CCR2B, NPR3, TRPV4, SEAP, and conservative amino acid substitution variants thereof.

The present invention also includes a method of identifying a cell that will express a protein-of-interest by a cell-of-interest including: operably linking (fusing) an oligonucleotide encoding a protein-of-interest to an oligonucleotide encoding a marker protein; introducing the fused oligonucleotide into a replicable vector; introducing the vector into a cell-of-interest; growing the cell-of-interest under conditions which bring about expression of a protein-of-interest; and measuring for expression of the marker protein.

BRIEF DESCRIPTION OF THE DRAWINGS

The foregoing summary, as well as the following detailed description of the invention, will be better understood when read in conjunction with the appended drawings. For the purpose of illustrating the invention, certain embodiment(s) are shown in the drawings. It should be understood, however, that the invention is not limited to the precise arrangements and instrumentalities shown. Drawings are not necessary to scale. Certain features of the invention may be exaggerated in scale or shown in schematic form in the interest of clarity and conciseness.

FIGS. 2A and 2B are images of TnT4 cells. FIG. 2A shows phase contrast images of TnT4 cells with cellular pleiomorphy. The bar represents 100 μm. FIG. 2B shows an enlarged portion of FIG. 2A with several cells in more detail. The bar represents 25 μm.

FIG. 3 is an image of an agarose gel showing DNA fingerprints of TnT4 and

Sf21 cells. Cell lines are indicated at the top of each lane; primer sets 1-3 (McIntosh et al. 1996) are indicated at the top of the panel; Lane "M" contains molecular size markers: and lanes labeled "N. C." have no DNA controls for each primer set.

Figure 4A:
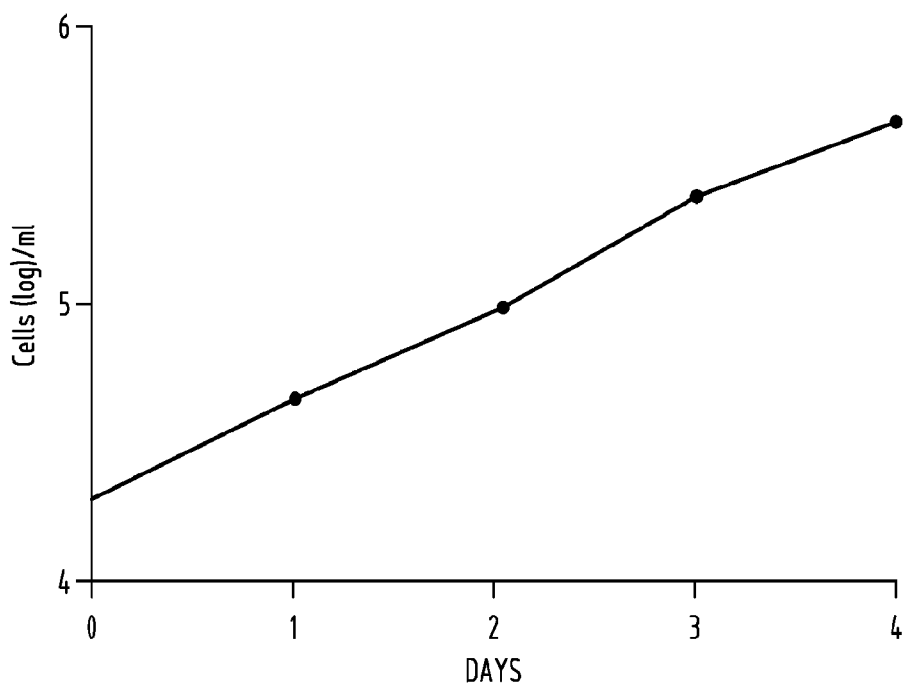
Figure 4B:
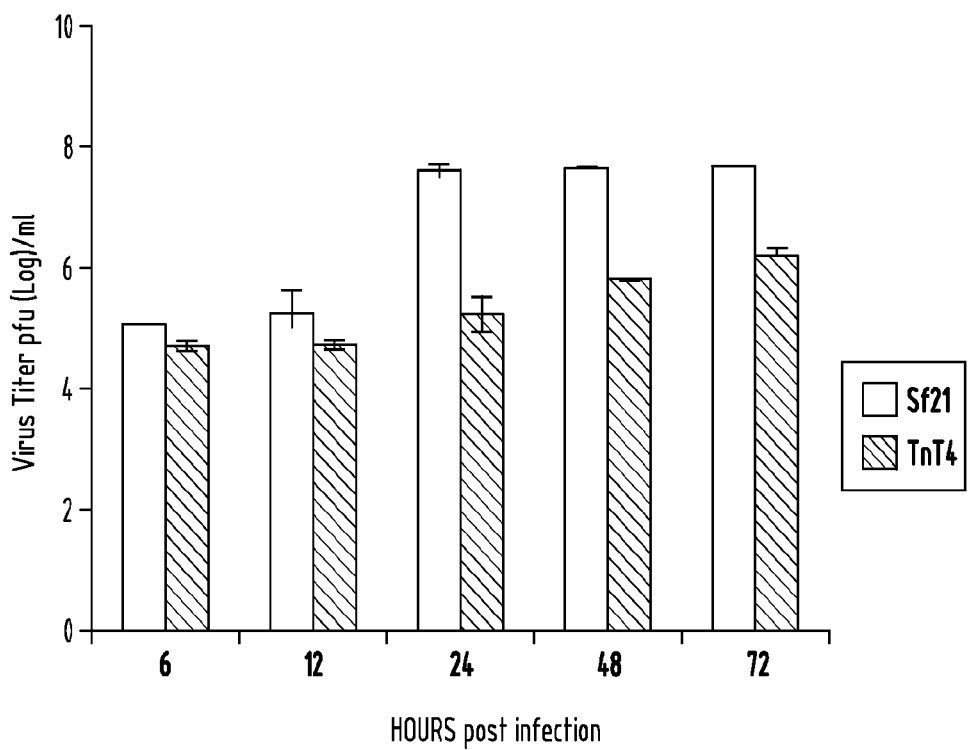
Figure 5A:
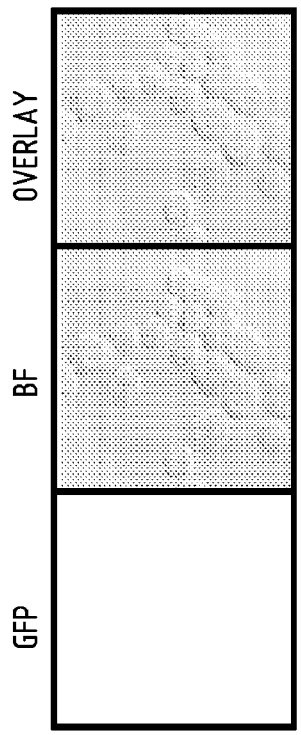
Figure 5B:
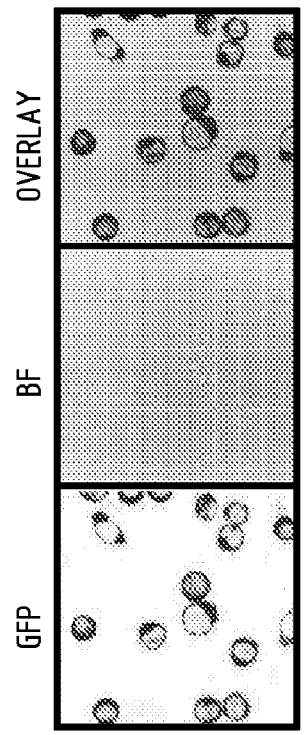
Figure 5C:
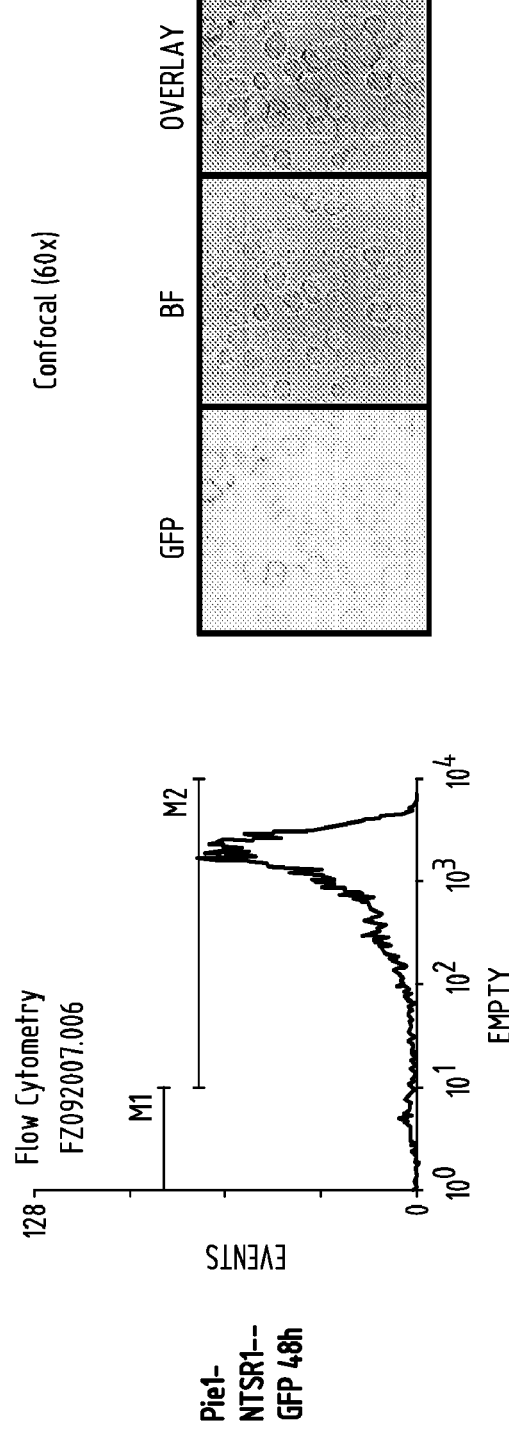
Figure 5D:
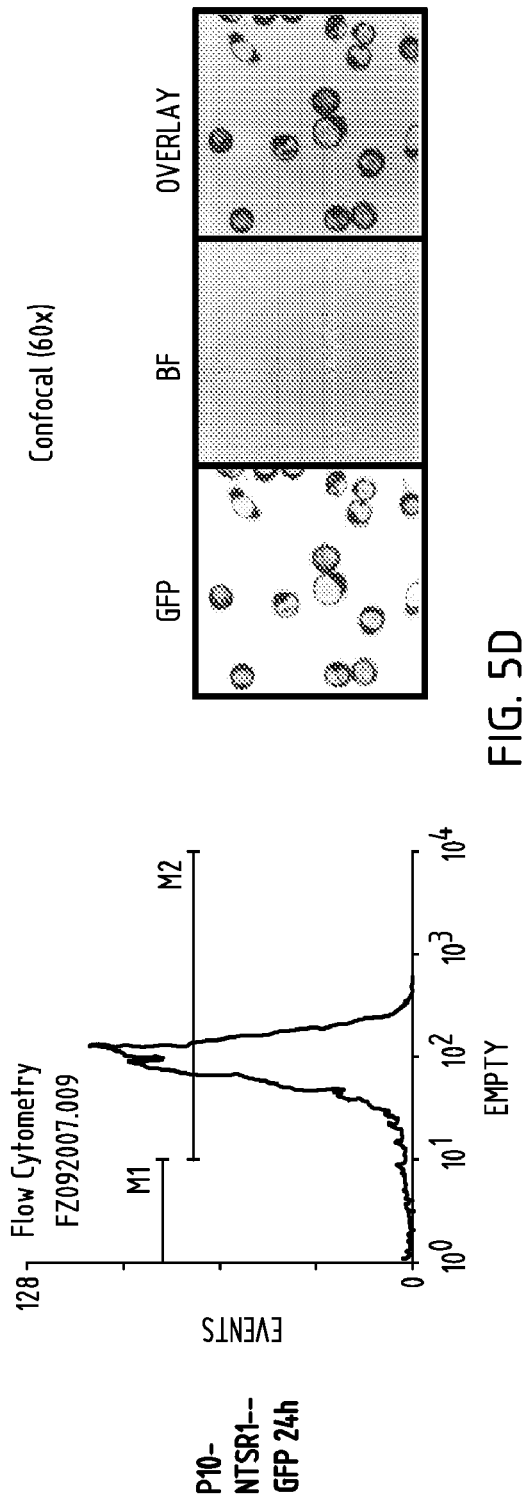
Figure 5E:
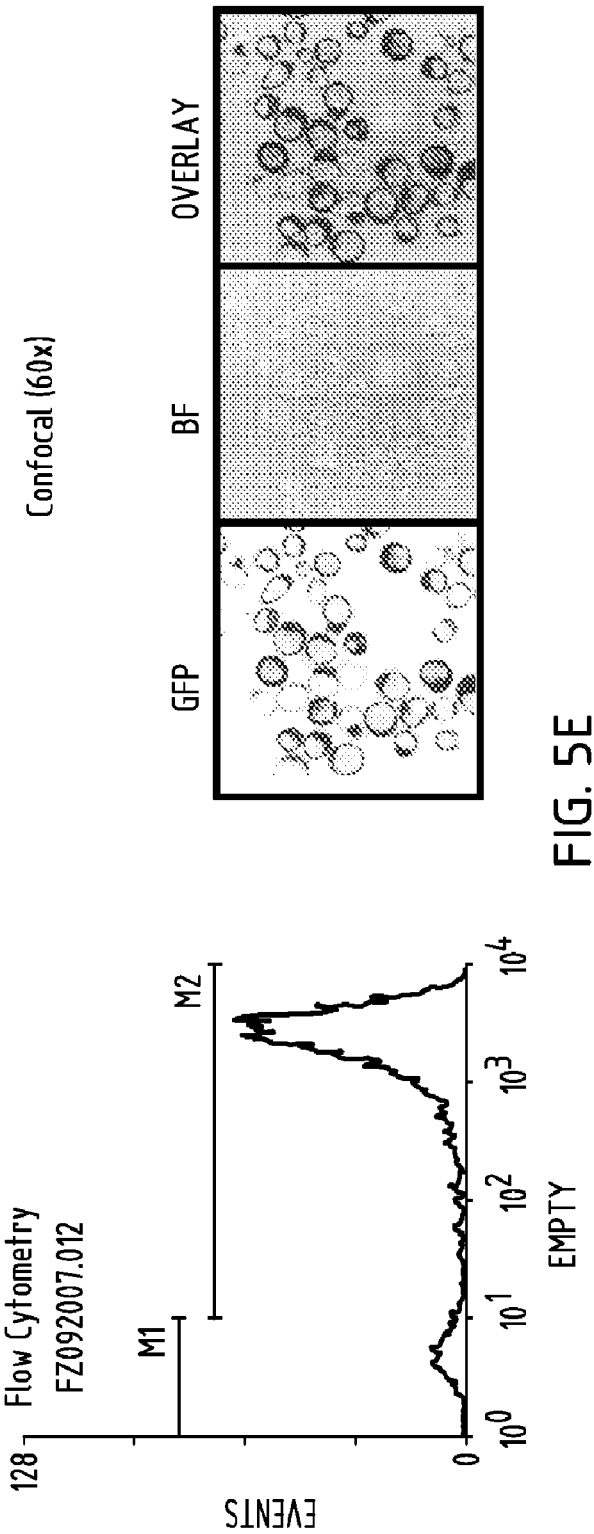

FIGS. 4A and 4B are graphs showing cell growth rates and virus production. Referring to FIG. 4A, cells were plated in 60 mm culture dishes in TC100 medium supplemented with 10% fetal bovine serum. Cells were scraped from the plates and counted using a hemocytometer. Cell counts were normalized based on the volume of medium per plate at the time of counting. Bars indicate standard deviation from two independent experiments. Referring to FIG. 4B, cells were infected with AcMNPV expressing β-galactosidase at an multiplicity of infection rate (moi) of 10 and supernatants were collected at the times indicated. Virus titers were determined by plaque assay. Sf21 cells are indicated by open bars and TnT4 cells by shaded bars. Bars indicating standard deviation are from two independent experiments.

FIGS. 5A-5E. Flow cytometry and confocal microscopy showed fluorescence from the expression of NTSR1-GFP in Sf21. Cells were mock infected (FIG. 5A) or infected by Pie-1-NTSR1-GFP (FIGS. 5B and 5C) or P10-NTSR1-GFP (FIGS. 5D and 5E) for 1 hr and replaced with fresh media. 24 hours (FIGS. 5B and 5D) or 48 hours (FIGS. 5C and 5E) post infection, cells were subjected to flow cytometry and confocal microscope analysis (magnification, 60×). Graphic plots of cell numbers and fluorescent intensity of GFP positive cells are shown for flow cytometry analysis in the first column. Confocal images of fluorescence, bright field (BF) images, and overlays of fluorescent and BF images are shown in the next three columns.

FIGS. 6A-6E. Flow cytometry and confocal microscopy showed fluorescence from the expression of NTSR1-GFP in TnT4 cells. Cells were mock infected (FIG. 6A) or infected by Pie-1-NTSR1-GFP (FIGS. 6B and 6C) or P10-NTSR1-GFP (FIGS. 6D and 6E) for 1 hr and replaced with fresh media. 24 hours (FIGS. 6B and 6D) or 48 hours (FIGS. 6C and 6E) post infection, cells were subjected to flow cytometry and confocal microscope analysis (magnification, 60×). Graphic plots of cell numbers and fluorescent intensity of GFP positive cells are shown for flow cytometry analysis in the first column. Confocal images of fluorescence, bright field (BF) images, and overlays of fluorescent and BF images are shown in the next three columns.

Figure 7A:
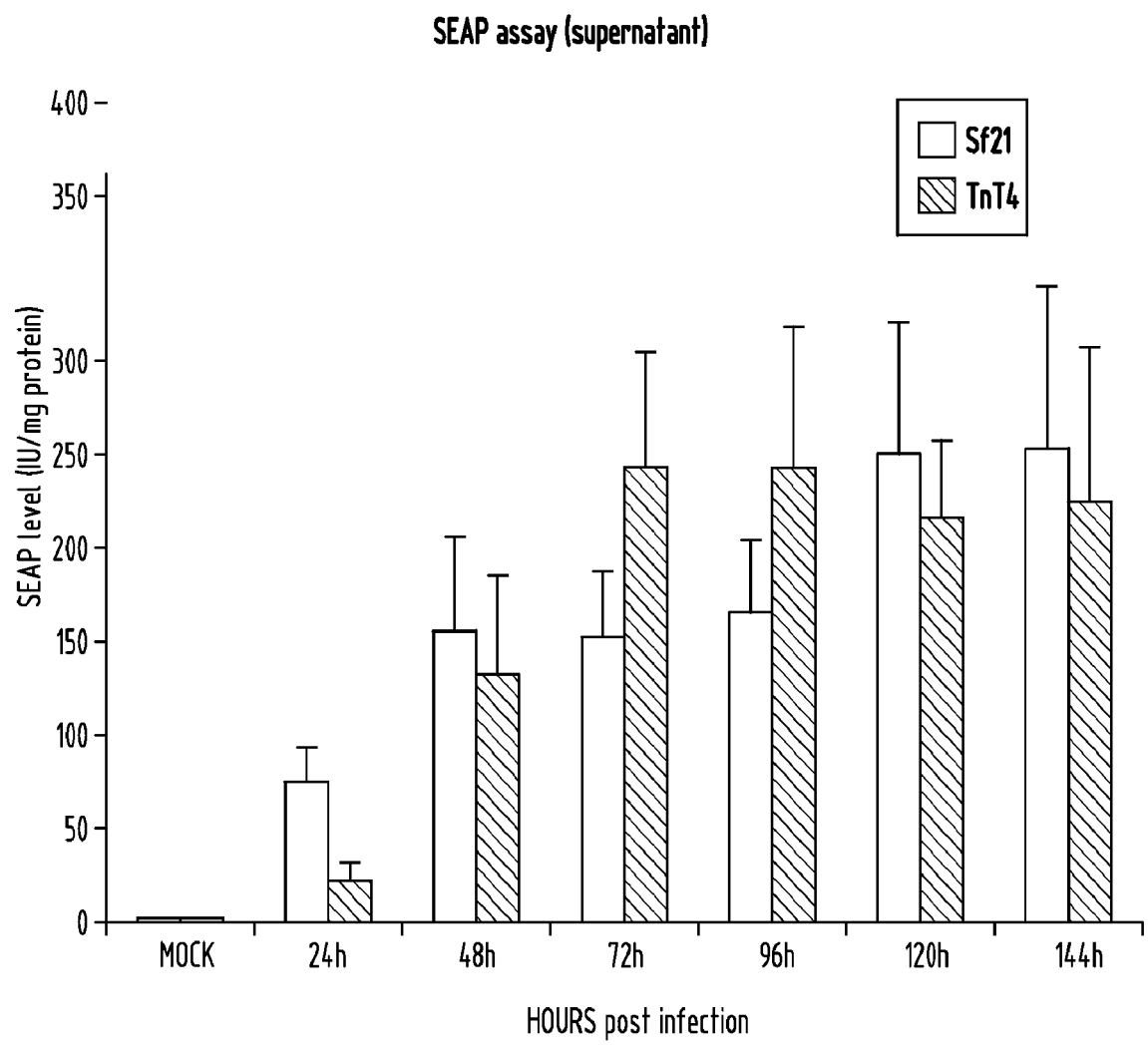
Figure 7B:
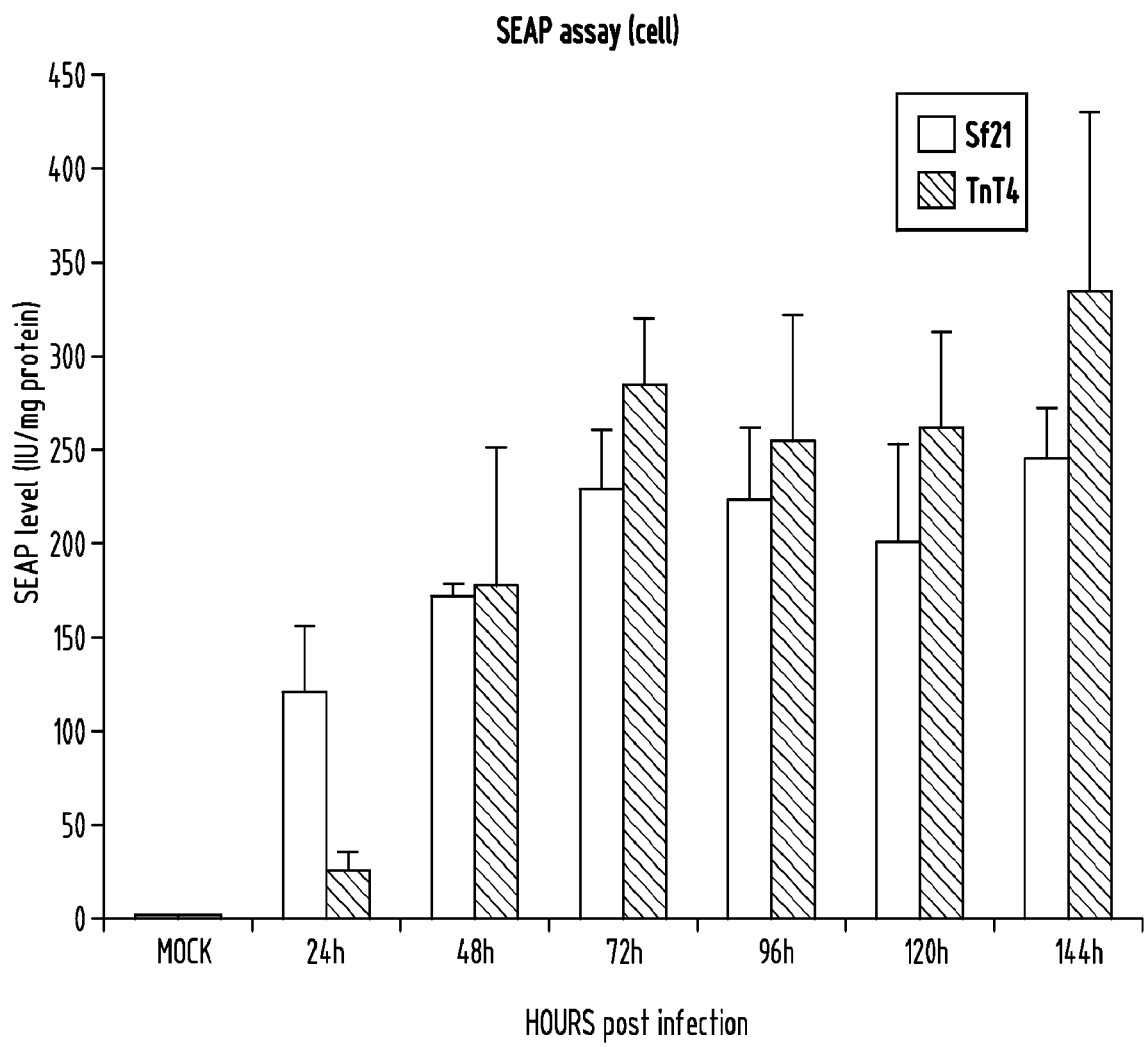

FIGS. 7A and 7B show secreted alkaline phosphatase (SEAP) levels from the supernatants and cells of Sf21 and TnT4 cell lines infected with AcMNPV-SEAP virus. Supernatants (FIG. 7A) and cells (FIG. 7B) were collected separately 24 hours-144 hours after infection. SEAP and protein levels were measured as described in Example 1 below. SEAP is expressed as IU/mg protein. Bars indicate the standard deviation from three independent experiments done in triplicate and *indicates there is significant difference between the Sf21 and TnT4 cells ($P=0.01$, t-test).

Figure 8:
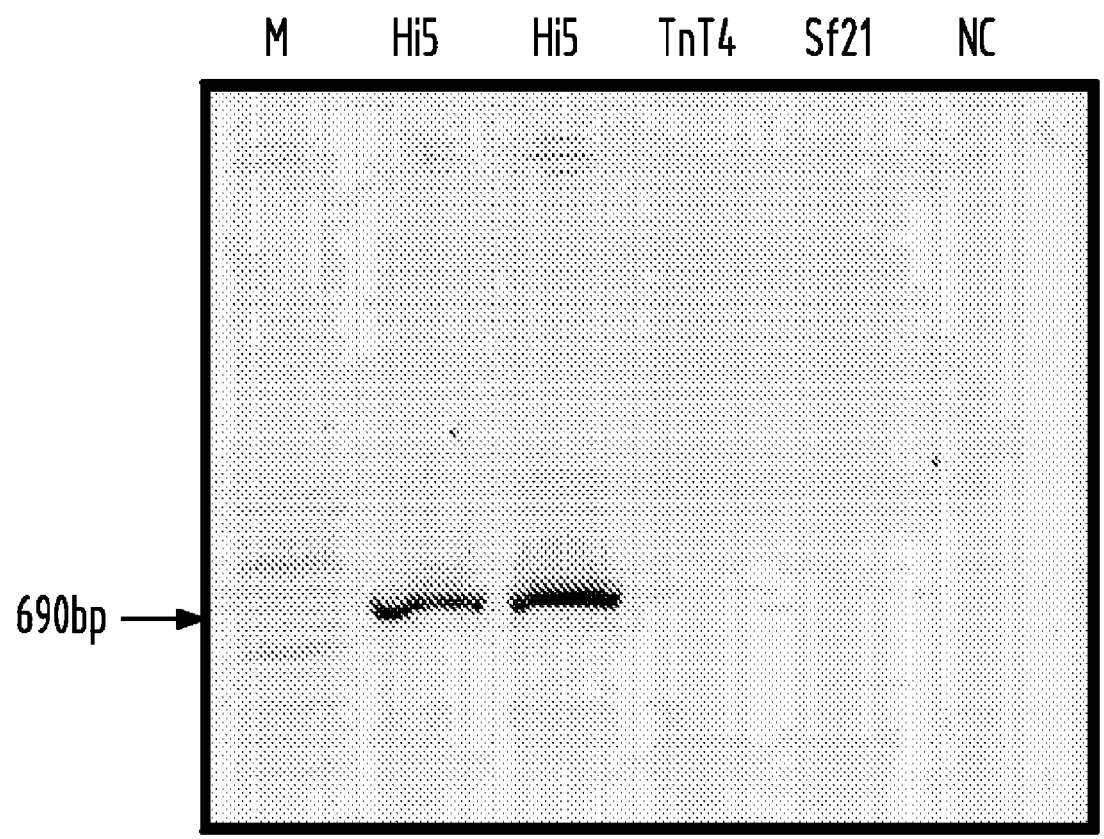

FIG. 8 shows PCR analysis of TnT4 cells for the presence of the latent nodavirus. RNA was isolated from Hi5, TnT4, and SF21 cells and used as template for cDNA synthesis and the cDNA was analyzed for the presence of nodavirus by PCR using the forward primer: 5'ACATCCAGATCCGAT-CAAGT3' (SEQ ID NO. 14) and the reverse primer: 5'GCCAGGAATGTTGCTTGCAA3 (SEQ ID NO. 15), as described by Li et al. The PCR products were resolved on an agarose gel. The 690 bp PCR product is diagnostic for the nodavirus.

Figure 9A:
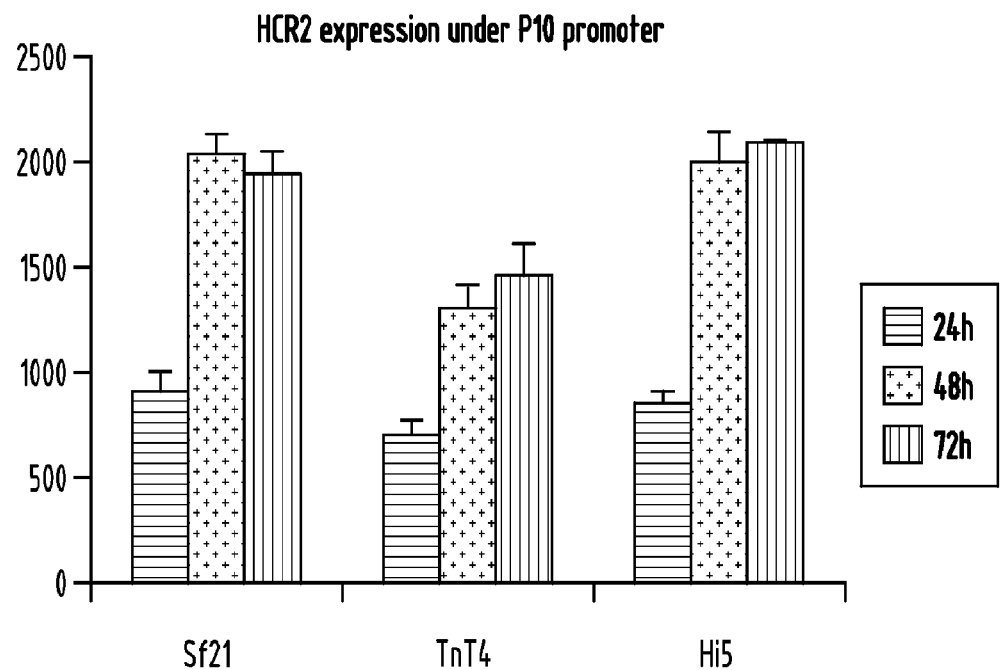
Figure 9B:
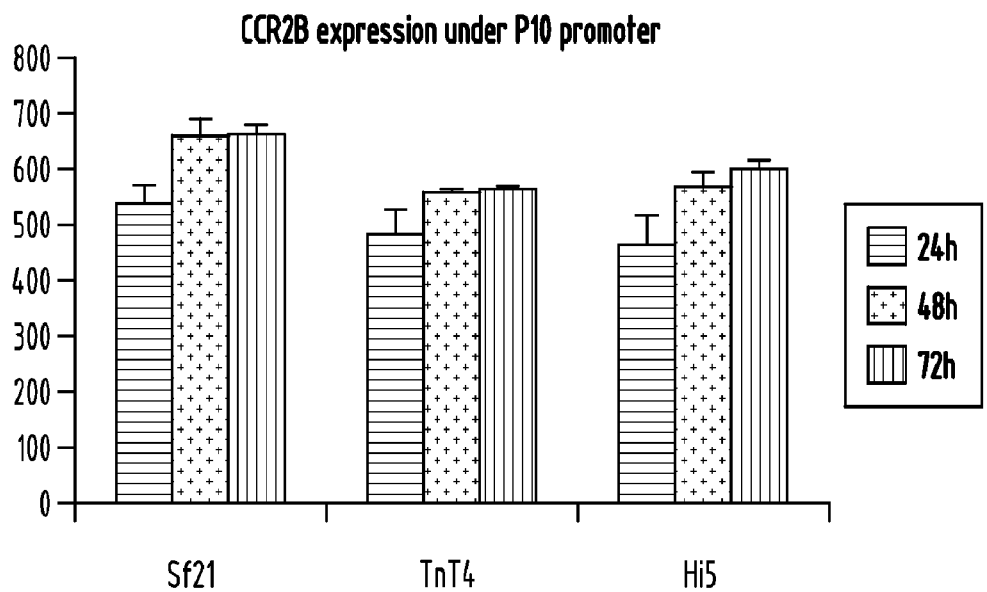
Figure 9C:
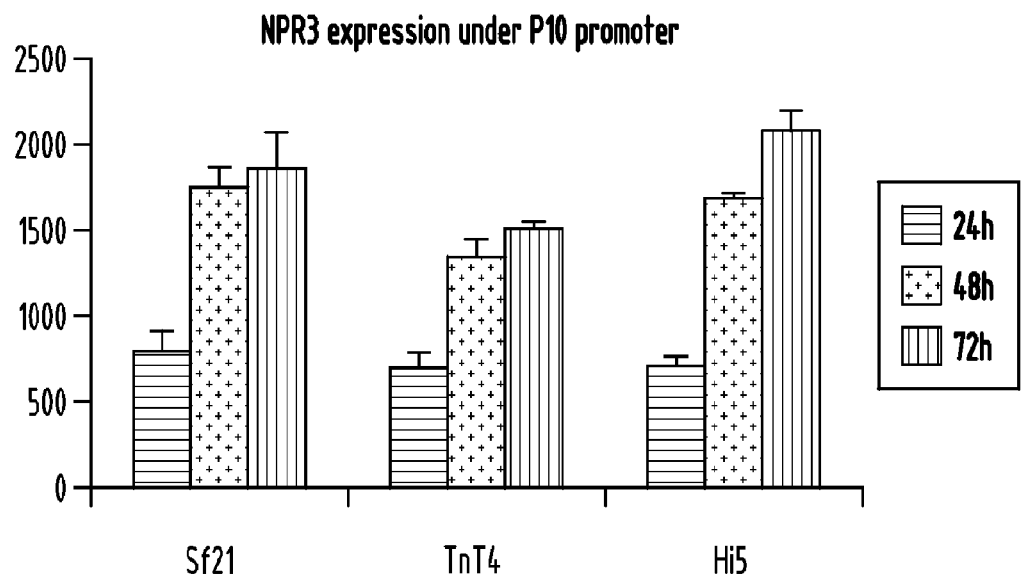
Figure 9D:
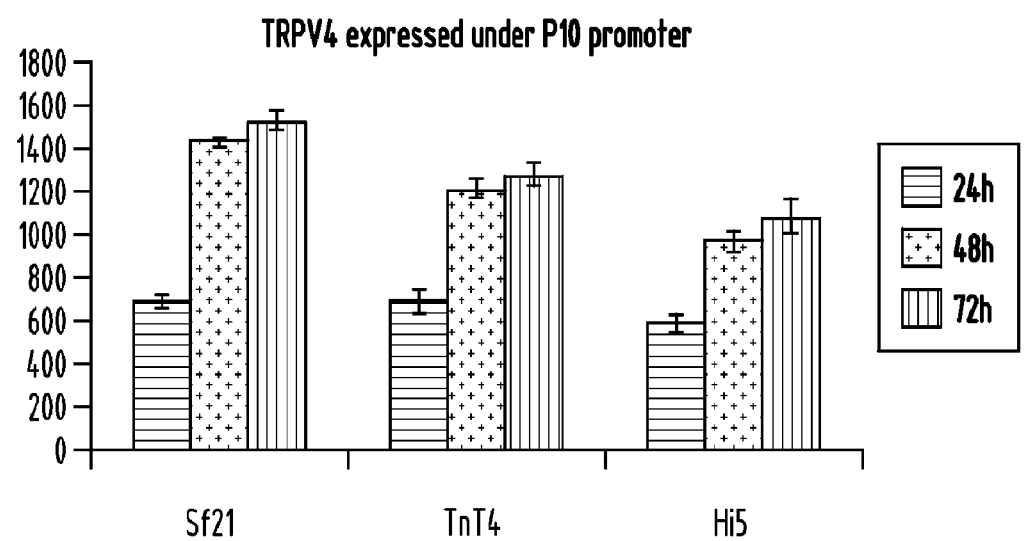

FIGS. 9A-9D show the relative fluorescence of baculovirus expressed GFP fusion proteins in Sf21, TnT4, and Hi5 cells over time (24, 48, and 72 hpi). FIG. 9A shows the relative fluorescence of human cannabinoid receptor 2; FIG. 9B shows the relative fluorescence of cytokine receptor 2B; FIG. 9C shows the relative fluorescence of natriuretic peptide receptor C; and FIG. 9D shows the relative fluorescence of transient receptor potential vanilloid 4 ion channel.

DETAILED DESCRIPTION OF THE PREFERRED EMBODIMENTS

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All references, patents, patent publications, articles, and databases, referred to in this application are incorporated herein by reference in their entirety, as if each were specifically and individually incorporated herein by reference. Such patents, patent publications, articles, and databases are incorporated for the purpose of describing and disclosing the subject components of the invention that are described in those patents, patent publications, articles, and databases, which components might be used in connection with the presently described invention.

The information provided below is not admitted to be prior art to the present invention, but is provided solely to assist the understanding of the reader.

The details of one or more embodiments of the invention are set forth in the accompanying drawings and the description below. Other features, embodiments, and advantages of the invention will be apparent from the description and drawings, and from the claims. The preferred embodiments of the present invention may be understood more readily by reference to the following detailed description of the specific embodiments and the Examples and Sequence Listing included hereafter.

The text file filed concurrently with this application, titled "MIC037 FP340AWO Sequence Listing.txt" contains material identified as SEQ ID NOS: 1-23, which material is incorporated herein by reference. This text file was created on Apr. 14, 2009, and is 63,973 bytes.

Unless defined otherwise, all technical and scientific terms used herein have the meaning commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document.

In this specification and the appended claims, the singular forms "a," "an" and "the" include plural reference unless the context clearly dictates otherwise.

The term "cell" is used in its usual biological sense, and does not refer to an entire multicellular organism. The cell can, for example, be in vitro, e.g., in cell culture. The term "cell" as used herein, refers to an isolated cell, as well as any individual cell, harvested cell, and culture containing a cell, so long as they are derived from a cell line. For example, TnT4 cells are cells derived from the TnT4 cell line.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "fusion protein" refers to a protein comprising amino acid sequences that are in addition to, in place of, less than, and/or different from the amino acid sequences encoding the original or native full-length protein or subsequences thereof. Moreover, a nucleic acid sequence or amino acid sequence of a first protein can be modified to include sequences that are substantially identical to the nucleic acid sequence or amino acid sequence, respectively, of a second protein and, thereby, a "fusion protein" is constructed.

The term "heterologous" when used with reference to portions of a nucleic acid or protein indicates that the molecule comprises two or more subsequences that are not found in the same relationship to each other in nature. For instance, a heterologous nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "host cell" includes an individual cell or cell culture which can be or has been a recipient of any recombinant vector(s). Host cells include progeny of a single host cell, and the progeny may not necessarily be completely identical (in morphology or in total DNA complement) to the original parent cell due to natural, accidental, or deliberate mutation and/or change. A host cell includes cells tranfected or infected in vitro with a recombinant vector. A host cell which comprises a recombinant vector or construct of the invention is a "recombinant host cell."

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. This definition also refers to the complement of a test sequence. Preferably, the percent identity exists over a region of the sequence that is at least about 25 amino acids in length, more preferably over a region that is 50 or 100 amino acids in length.

For sequence comparison, one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homolog aliment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351 360 (1987). The method used is similar to the method described by Higgins & Sharp, CABIOS 5:151 153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nucleic Acids Res. 12:387 395 (1984)).

Another example of algorithm that is suitable for determining percent sequence identity and sequence similarity is the BLAST algorithm, which is described in Altschul et al., J. Mol. Biol. 15:403 410 (1990). Software for performing BLAST analyses is publicly available through the National Center for Biotechnology Information (ncbi.nlm,nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., sugar). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873 5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "substantially identical," in the context of two nucleic acids or polypeptides, refers to two or more sequences or subsequences that have at least 60%-70%, preferably 80-85%, more preferably 90-95%, or most preferably 96%, 97%, 98%, or 99% nucleotide or amino acid identity, when compared and aligned for maximum correspondence, as measured using one of the above-identified sequence comparison algorithms or by visual inspection. Preferably, the substantial identity exists over a region of the sequences that is at least about 50 nucleotides or residues in length, more preferably over a region of at least about 100 nucleotides or residues, and most preferably the sequences are substantially identical over at least about 150 nucleotides or residues. In a most preferred embodiment, the sequences are substantially identical over the entire length of the coding regions. An indication that two nucleic acid sequences are substantially identical is that the two molecules or their complements hybridize to each other under stringent conditions, or can be amplified by the same primer set. Another indication that two nucleic acid sequences are "substantially identical" is that the polypeptide encoded by the first nucleic acid is immunologically cross reactive with the antibodies raised against the polypeptide encoded by the second nucleic acid.

As used herein the term "isolated," in the context of a subject isolated cell, refers to a cell that is in an environment different from that in which the cell naturally occurs. As used herein, the term "clonal cell line" refers to a cloned cell line that is typically immortalized, e.g., under suitable in vitro culture conditions, the cell line divides virtually indefinitely. Isolated cells may also include "host cells."

"Nucleic acid" refers to deoxyribonucleotides or ribonucleotides and polymers thereof in either single- or double-stranded form. The term encompasses nucleic acids containing known nucleotide analogues or modified backbone residues or linkages, which are synthetic, naturally occurring, and non-naturally occurring, which have similar binding properties as the reference nucleic acid, and which are metabolized in a manner similar to the reference nucleotides. Examples of such analogues include, without limitation, phosphorothioates, phosphoramidates, methyl phosphonates, chiral-methyl phosphonates, 2-O-methyl ribonucleotides, peptide-nucleic acids (PNAs). Unless otherwise indicated, a particular nucleic acid sequence also implicitly encompasses variants thereof (e.g., degenerate codon substitutions that encode the same amino acids) and complementary sequences, as well as the sequence explicitly indicated. The term "nucleic acid" is used interchangeably with gene, cDNA, mRNA, oligonucleotide, and polynucleotide.

The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences.

The terms "polypeptide," "peptide," and "protein" are used interchangeably herein to refer to a polymer of amino acid residues. These terms also include amino acid polymers in which one or more amino acid residue is an analogue or mimetic of a corresponding naturally occurring amino acid, as well as to naturally occurring amino acid polymers. For a detailed description of protein chemistry and structure, see Schulz, GE et al., Principles of Protein Structure, Springer-Verlag, New York, 1978, and Creighton, T. E., Proteins: Structure and Molecular Properties, W. H. Freeman & Co., San Francisco, 1983, which are hereby incorporated by reference.

The term "recombinant" when used with reference, e.g., to a cell, nucleic acid, vector, or protein indicates that the cell, nucleic acid, or vector has been modified by the introduction of a heterologous nucleic acid or the alteration of a native nucleic acid, or that the cell is derived from a cell so modified, or that the protein is encoded or expressed by such a nucleic acid or cell. Thus, for example, recombinant cells express genes and proteins that are not found within the native (non-recombinant) form of the cell or express native genes and proteins that are otherwise abnormally expressed, under expressed or not expressed at all.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 15° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65. degree. C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

A "promoter sequence" is a DNA regulatory region capable of binding RNA polymerase in a cell and initiating transcription of a downstream (3<1>direction) coding sequence For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase Eukaryotic promoters will often, but not always, contain "TATA" boxes and "CAT" boxes. Prokaryotic promoters contain Shine-Dalgamo sequences in addition to the −10 and −35 consensus sequences An "expression control sequence" is a DNA sequence that controls and regulates the transcription and translation of another DNA sequence A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell Signal sequences can be found associated with a variety of proteins native to prokaryotes and eukaryotes The present invention includes a new cell line established from Lepidopteran embryos. In particular, the present invention includes a cell line for use in BEVS, identified as "MSU-TnT4" (or "TnT4"), derived from *Trichoplusia ni* embryos.

This cell line has good growth characteristics and expresses various human proteins to high levels (e.g., membrane proteins). Such proteins include, but are not limited to: human neurotensin receptor 1 (NTSR1), a model G-protein coupled receptor; G-protein coupled receptors human cannabinoid receptor 2 (hCR2) and cytokine receptor 2B (CCR2B); a highly glycosylated single membrane spanning protein known as natriuretic peptide receptor C (NPR3); an ion channel known as transient receptor potential vanilloid 4 (TRPV4), and secreted alkaline phosphatase (SEAP). It is expected that the TnT4 cell line also will show good growth characteristics in BEVS with other proteins (e.g., membrane proteins).

Figure 6A:
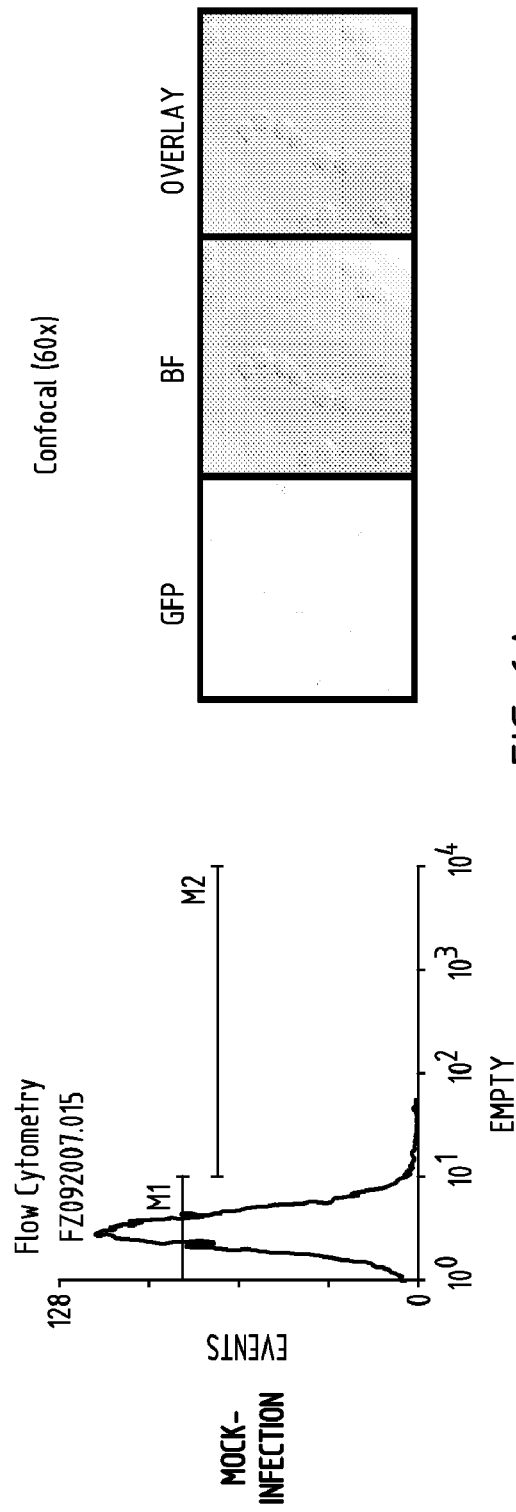
Figure 6B:
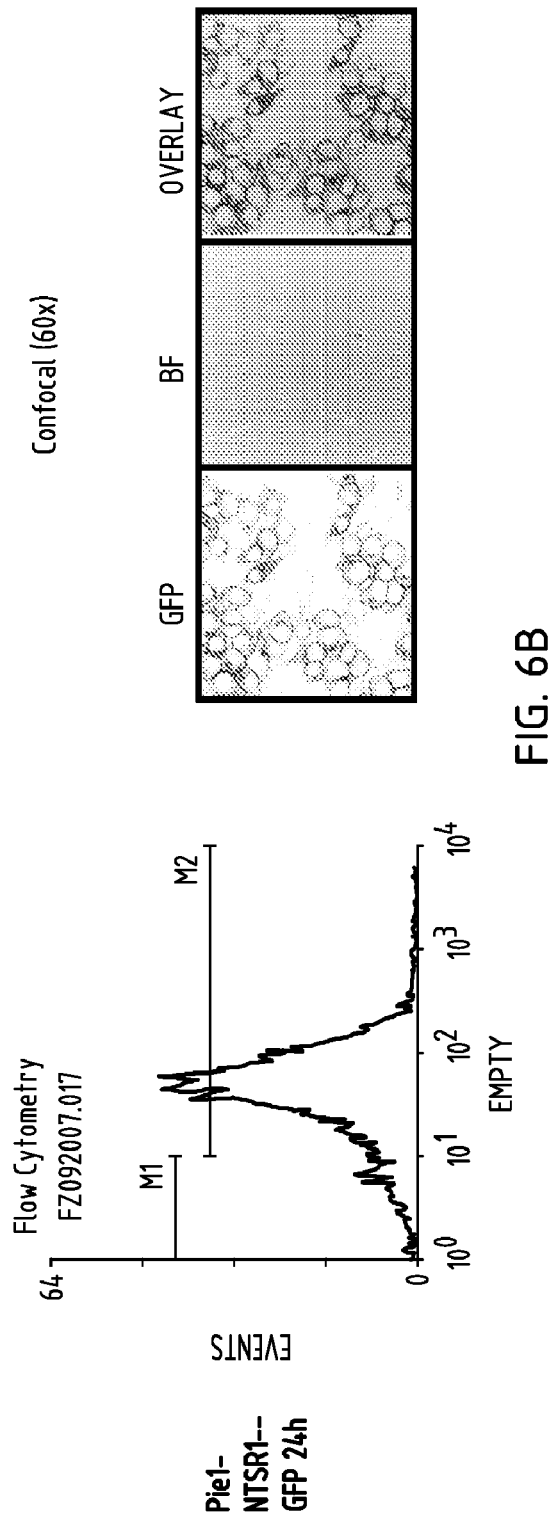
Figure 6E:
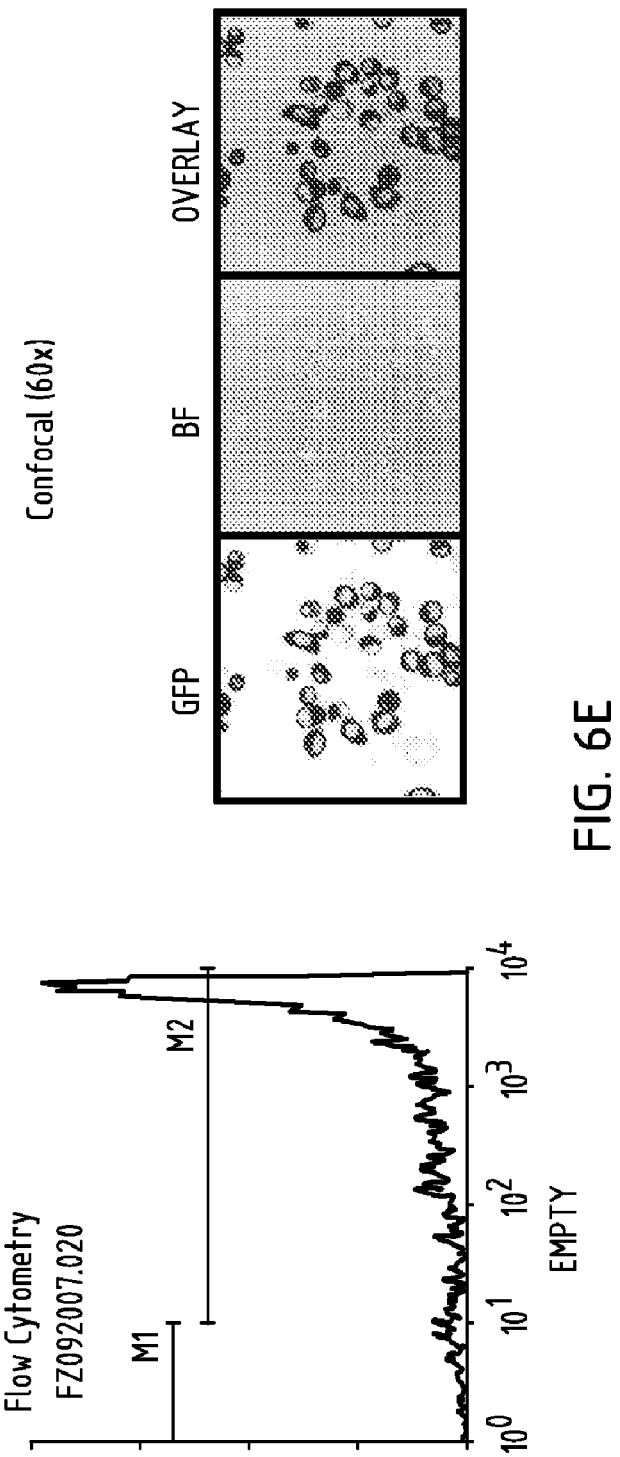

TnT4 cells grow rapidly and can be grown in suspension culture. TnT4 cells are susceptible to infection by AcMNPV and support its complete lifecycle, producing both BV and polyhedra (FIGS. 6D and 6E). However, in contrast to Hi-5 cells (Granados et al. 1994), a commercially available T ni cell line, TnT4 cells produce less BV than Sf21 cells (FIG. 4B).

Analysis of fluorescence by flow cytometry and confocal microscopy showed that TnT4 cells supported significantly higher levels of NTSR1-GFP production than Sf21 cells at 48 hours post-injection from the P10 promoter and at 24 hours post-injection from the ie-1 promoter (FIGS. 5 and 6, Table 1). Table 1 shows the percentage and average intensity of GFP+ positive cells from Sf21, TnT4 and Hi-5 cells from flow cytometry analysis:

suggests that reduced protein synthesis from the weaker and earlier ie-1 promoter facilitates protein trafficking These observations support the idea that although strong, late baculovirus promoters, such as the P10 and polyhedrin promoters, can drive high levels of protein synthesis, this level of expression may overwhelm protein folding and modification in the RER and Golgi.

The inventors also have shown the expression of additional proteins using BEVS in the TnT4 cell line and compared such expression to comparative expression data to BEVS in Sf21 and Hi5 cells. These proteins were expressed using a p10 promoter and the expression compared using fluorescent intensity for GFP. These additional proteins include two more G-protein coupled receptors (human cannabinoid receptor 2 (hCR2) and cytokine receptor (CCR2B)), a highly glycosylated single membrane spanning protein (natriuretic peptide receptor C (NPR3), and an ion channel (the transient receptor potential vanilloid 4 (TRPV4). The methods of analysis for these membrane proteins are described in Example 6 below. Further, Table 1 shows the numerical data for the 72 h time point. (Three time points of the same data are shown graphically in FIGS. 9A-9D.) Table 1 shows the relative fluorescence of these four membrane protein GFP fusions expressed from baculovirus in Sf21, TnT4, and Hi5 cells at 72 hpi from captured images analyzed by Metamorph software.

TABLE 1

| | Sf21 | | TnT4 | | Hi-5 | |
|---|---|---|---|---|---|---|
| | GFP+ cells percentage (%) | Median Intensity of GFP | GFP+ cells percentage (%) | Median Intensity of GFP | GFP+ cells percentage (%) | Median Intensity of GFP |
| Mock | 0.28 | 18.7 ± 4.5 | 0.24 | 17.9 ± 4.3 | 0.3 | 18.6 ± 8.1 |
| Pie1-NTSR1-GFP 24 h | 21.69 | 43.4 ± 5.1 | 77.04 | 71.6 ± 13.0* | 94.42 | 71.3 ± 16.2 |
| Pie1-NTSR1-GFP 48 h | 91.38 | 125.2 ± 30.1 | 96.91 | 87.2 ± 18.7 | 96.93 | 88.8 ± 27.8 |
| P10-NTSR1-GFP 24 h | 97.36 | 2027.9 ± 538.4 | 93.51 | 1120.1 ± 854.5 | 97.29 | 2961.0 ± 244.5 |
| P10-NTSR1-GFP 48 h | 97.49 | 3450.2 ± 450.5 | 98.08 | 6343.3 ± 641.4[§1] | 97.31 | 6219.5 ± 984.8[§2] |

*Significant difference compared to Sf21 cells, P = 0.028 t-test;
§Significant difference compared to Sf21 cells, [§1]P = 0.004 t-test; [§2]P = 0.03 t-test Analysis of expression in Hi-5 cells by flow cytometry showed similar expression levels as TnT4 cells. Interestingly, the fluorescent intensity increased dramatically in both TnT4 and Hi-5 cells relative to Sf21 cells between 24 and 48 h when NTSR1-GFP was expressed from the p10 promoter, suggesting a possible species difference in either the response to protein expression directly or indirectly due to species specific cellular responses to baculovirus infection (Chen and Thiem 1997; Clem et al. 1991; Lu and Miller 1996). Although higher protein expression was achieved with the p10 promoter in both cell lines, NTSR1-GFP was observed throughout the interior of the cell by confocal imaging, suggesting it was retained in intracellular membranes (FIGS. 5 and 6). Expression from the ie-1 promoter was lower but NTSR1-GFP appeared to localize to the cytoplasmic membrane in both Sf21 and TnT4 cells (FIGS. 5 and 6). This observation remains to be confirmed by more definitive techniques such as co-localization with cytoplasmic membrane markers, but

TABLE 1

| | Sf21 | TnT4 | Hi5 |
|---|---|---|---|
| hCR2 | 1950 ± 106 | 1471 ± 147 | 2091 ± 16 |
| CCR2B | 664 ± 21 | 572 ± 1 | 607 ± 15 |
| NPR3 | 1857 ± 204 | 1522 ± 33 | 2088 ± 104 |
| TRPV4 | 1511 ± 59 | 1274 ± 64 | 1073 ± 97 |

Based on this data, the inventors believe TnT4 is capable of being used with BEVS to express human G-protein coupled receptors, and various other proteins (e.g., membrane proteins).

Further, it appears that the Hi5 cell line (BTI-TN-5B1-4), which is derived from *Trichoplusia ni* embryos, harbors a latent nodavirus (Li T-C et al., 2007, Latent Infection of a New Alphanodavirus in an Insect Cell Line, *J. Virol.* 81:10890-10896). A nodavirus is a bipartite positive sense RNA virus, many of which infect insects and a few infect mammals. Also, a nodavirus is a small icosahedral virus that does not have an envelope. The particular nodavirus (reported by Li, et al.) in the Hi5 cell line is related to the Flockhouse virus, a nodavirus that was originally isolated from grass grubs in New Zealand but which can replicate in other organisms such as plants, nematodes, and mammals. The inventors used the PCR primers (SEQ ID NO. 14-15) and cycling parameters described in this Li et al paper to analyze TnT4 cells for the nodavirus. The results show that the TnT4 cell line is not infected with the nodavirus (see, FIG. 8). In view of the absence of infection by the nodavirus, the TnT4 cell line has further value as a host cell for use in connection with BEVS in the production of proteins that have not been exposed to the nodavirus.

Also, the present invention includes a method of identifying a cell that will express a protein-of-interest, or highly express a protein-of-interest, by a cell-of-interest including the following steps: operably linking (fusing) an oligonucleotide encoding a protein-of-interest to an oligonucleotide encoding a marker protein; introducing the fused oligonucleotide into a replicable vector (e.g., BEVS), introducing the vector into a cell-of-interest, growing the cell-of-interest under conditions which bring about expression of a polypeptide encoded by the oligonucleotide, and measuring for the presence of the marker protein. For example, expression of the G-protein coupled receptor, NTSR1 as a C-terminally tagged GFP fusion protein in a recombinant baculovirus can be used as a tool for analyzing protein synthesis in insect cells. Previous studies indicate that yields of baculovirus-expressed G-protein coupled receptors, and other membrane proteins, vary considerably (Akermoun et al. 2005; Grisshammer and Tate 1995; Massotte 2003; Sarramegna et al. 2003). The general approach of using fluorescent protein fusions is relatively rapid and will be useful for testing the expression of other proteins in other cell lines. Thus, using this approach, other lepidopteran insect cell lines (that have been developed for studies of insect pathogens and insect physiological processes) can be screened for their utility for expressing proteins. In addition, this approach can be used to evaluate other parameters needed for optimal protein production, such as promoters, signal sequences, the addition of chaperones, virus modifications, media composition, and growth conditions.

The importance of analyzing different insect cell lines for their ability to express a particular protein is well established (Davis et al. 1993; Hink 1991; McKenna et al. 1998; Wickham et al. 1992). No presently commercially available cell line appears to be superior for all proteins. TnT4 cells are a good addition to the selection of available cell lines for recombinant protein production, in particular, for protein production.

The invention also provides a method of producing polypeptides by introducing an oligonucleotide into a replicable vector (e.g., BEVS), introducing the vector into a TnT4 host cell, and growing the host cell under conditions which bring about expression of a polypeptide encoded by the oligonucleotide. The polypeptide then may be recovered from the host cell. Methods for producing polypeptides from a cell are generally known and these methods can be applied to the production of proteins using BEVS in the present TnT4 cell line. For specific examples of such protein production methods see: O'Reilly D R, Miller L K, Luckow V. 1992. Baculovirus Expression Vectors: A Laboratory Manual. New York, W. H. Freeman and Company. ISBN 0-19-509131-0; and Murhammer D W (ed). 2007. Baculovirus and insect cell expression protocols, 2nd ed, Methods in Molecular Biology (Clifton N.J.) vol. 388, Totowa, N.J., Humana. ISBN 1588295370, 9781588295378.

More specifically, vectors may be introduced into the TnT4 host cell to provide for expression of any polypeptide (e.g. NTSR1, hCR2, CCR2B, NPR3 and TRPV4) or a conservative amino acid substitution variant thereof. For example, a conservative amino acid substitution variant may differ from the original sequence such that it has 90%, 95%, 96%, 97%, 98% or 99% identity with the original amino acid sequence of the polypeptide. It is well known in the art that the amino acids within the same conservative group can typically substitute for one another without substantially affecting the function of a protein. Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu.

The introduction of vectors into a host cell may be followed by causing or allowing expression from the nucleic acid, e.g. by culturing host cells (which may include cells actually transformed although, more likely, the cells will be descendants of the transformed cells) under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers.

In another embodiment, the oligonucleotide in the vector is operably linked to a control sequence which is capable of providing for the expression of the coding sequence by the host cell, i.e. the vector is an expression vector. In a further embodiment, the oligonucleotide in the vector is operably linked to a marker protein, such as GFP, to measure expression of the protein encoded by the oligonucleotide. Suitable vectors can be chosen or constructed, containing appropriate regulatory sequences, including promoter sequences, terminator fragments, polyadenylation sequences, enhancer sequences, marker genes and other sequences as appropriate. Promoters and other expression regulation signals may be selected to be compatible with the TnT4 host cell. Such promoters are readily available in the art.

When using a vector (e.g., BEVS) in a host cell to produce a protein, the protein may be either expressed alone or with some type of tag that can be later removed by proteolytic cleavage. For example, such a tag could be used to facilitate downstream purification of the protein. If a protein is to be expressed with a tag at the C-terminus, then a stop codon is included at the end of the coding sequence for the tag (rather than at the end of the coding sequence for the protein).

The vectors may be provided with an origin of replication, optionally a promoter for the expression of the oligonucleotide and optionally a regulator of the promoter. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell. Systems for cloning and expression of a polypeptide in a variety of different host cells are well known.

Having now generally described the invention, the same will be more readily understood through reference to the following examples, which are provided by way of illustration, and are not intended to be limiting of the present invention, unless specified.

EXAMPLES

Example 1

Materials and Methods for Examples 2-5

Establishment of Cell Lines

*T. ni* eggs were obtained from Lloyd Browne, Entopath Inc., Easton, Pa. Embryonic tissues were prepared essentially as previously described (Lynn 1996, 2001). Briefly, eggs were surface sterilized with 0.05% sodium hypochlorite for five minutes, followed in succession by one five minute wash each in 70% ethanol, sterile distilled water, phosphate buffered saline (O'Reilly et al. 1992), and tissue culture medium. The embryos were then dissociated from the eggs into TC 100 (JRH Bioscience, Lenexa, Kans.) tissue culture medium, supplemented with 10% fetal bovine serum (Hyclone Laboratories), 100 U/ml penicillin, 100 µg/ml streptomycin, and 0.25 µg/ml amphotericin B. Pools of approximately 20 embryos were minced with a scalpel and transferred to disposable $T_{12.5}$ flasks in 2 ml of medium supplemented as above. Cells were incubated at 27° C. Cells were monitored and fed every 7 days replacing half the media until cells proliferated and became confluent. Cells were then split 1:1 when they became confluent, until they were being split once a week, and as growth rates accelerated the split ratio was gradually increased to 1:8 per week and subsequently the cells were split twice a week. The growth rate continued to increase such that those cells were eventually maintained at a split ratio of 1:14 twice a week.

DNA fingerprinting. DNA was extracted from Sf21 and TnT4 cells respectively using Qiagen DNeasy Tissue Kit. For each PCR reaction, 150 ng DNA was used as template for a total volume of 25 ul reaction mix. Three sets of primers were used for the fingerprint as previously described (McIntosh et al. 1996). Each set of amplifications consisted of a negative control including distilled water instead of DNA sample as the template. Amplification was conducted under following conditions: 3 min of initial denaturation at 95° C., followed by forty cycles of denaturation at 95° C. for 30 s, annealing at 40° C. for 30 s and extension at 72° C. for 45 s. A final 72° C. extension was conducted for 10 min to stop the reaction. 10 ul of PCR products were loaded on a 2% agarose gel for electrophoresis.

Cell growth and virus production. Cells were laid down in 60 mm plates at $1.25 \times 10^5$ cells/plate, in duplicate, for each time point. Every 24 h the cells were scraped from two plates and counted using a hemocytometer and an inverted microscope. The number of cells per plate was calculated by multiplying by the volume of medium in the plate, as determined by weight, at the time of the counts. Counts were stopped when the cells reached confluence. Doubling times were calculated using standard methods (Kuchler 1977). Virus production was determined by infecting $1.5 \times 10^6$ cells per plate with recombinant AcMNPV, expressing β-galactosidase from the polh promoter, at an moi of 10. Supernatants were harvested at 6, 12, 24, 48, and 72 h pi and virus titers determined by plaque assay. The chromogenic indicator X-gal was included in the overlays at 120 µg/ml to facilitate plaque counts.

Recombinant baculovirus construction. Recombinant reporter viruses expressing a model membrane protein the G-protein coupled receptor, NTSR1, (Genbank accession number NM_002531) fused to enhanced green fluorescent protein (GFP) (Clontech, Mountain View, Calif.) was constructed to select and evaluate cell lines for enhanced protein production. The fusion proteins were expressed from either the AcMNPV p10 or ie-1 promoter, P10-NTSR1-GFP and Pie 1-NTSR1-GFP, respectively. NTSR1 was PCR amplified from a cDNA clone using NTSR1 F and NTSR1R (Table 2). Table 2 shows the oligonucleotides used in this study* (SEQ ID NOs: 3-14).

TABLE 2

| Primer name | Primer sequence (5'-3') | SEQ ID NOS: |
|---|---|---|
| NTRS1F | ATGCACTAGTAAAGAATTCACC ATGCGCCTCAACAGCTCCGCGC | 2 |
| NTRS1R | GGTAAAGCTTAAACCGGTAG CGTCTCGCGGGTGGCATTG | 3 |
| GFPF | TCCACCGGTCGCCACCA TGGTGAGCAAGGGCGAG | 4 |
| GFPR | GATAAAGCTTATAAGATCTAT ATTACTTGTACAGCT | 5 |
| Acp10F | GTTGGAGTCTAGAGTGCTATTTTACAAAG | 6 |
| Acp10R | GATTGGAATTCAAATGTAATTTACAGTATAG | 7 |
| Acie-1F | AAGCTTCTAGAATCCGCTCACCAAACG | 8 |
| Acie-1R | TTTGCGTCATAGTGAATTCGTTGTTC | 9 |
| GFP seq | CCGTCCTCCTTGAAGTCGATGCC | 10 |
| NTRS1$_1$ seq | ACGGTGCATTACCACCTGGGCAGCC | 11 |
| NTRS1$_2$ seq | ACCATCATCGCCAACAAGCTGACCGTCATG | 12 |
| NTRS1$_3$ seq | CAGGAGGAAGAGGCCAGCCTTCTCG | 13 |

*introduced restriction sites and restriction site sticky-ends are underlined.

Figure 1:
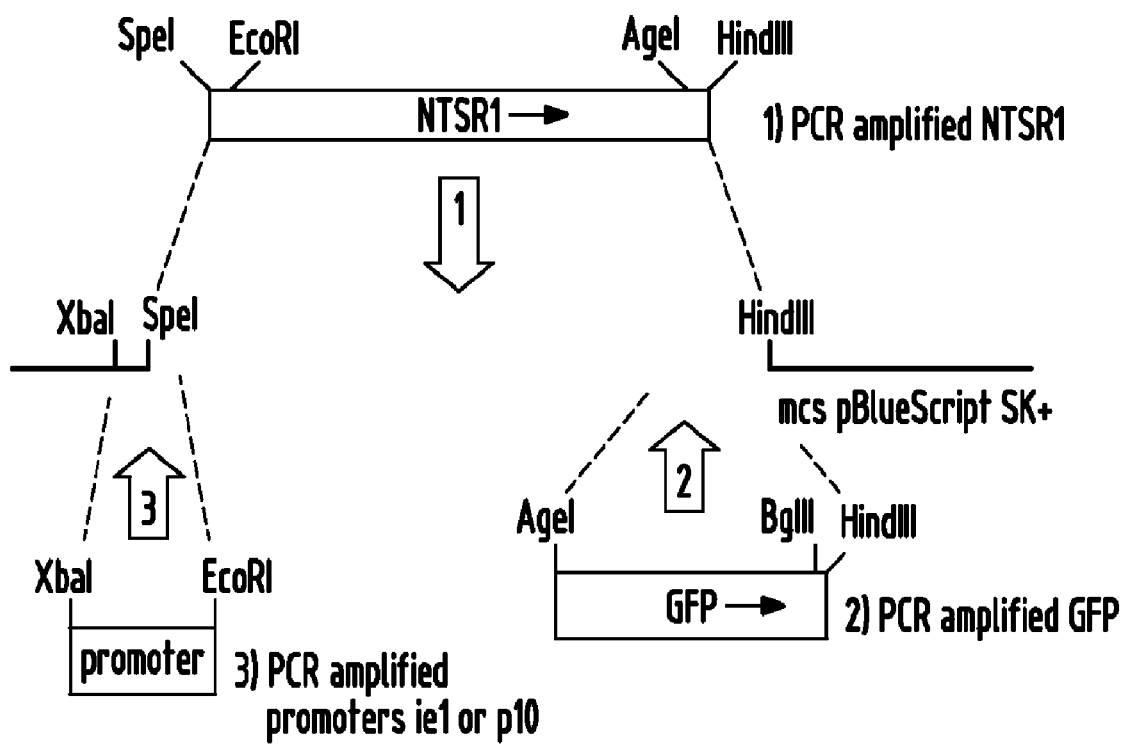
FIG. 1 is a schematic drawing showing the construction of the NTSR1-GFP reporter virus. NTSR-1, GFP, and baculovirus promoters were amplified by PCR, introducing suitable restriction sites for cloning. The promoter-fusion protein construct was assembled sequentially in pBluescriptSK+, in the order indicated in the schematic drawing. PCR and sequencing primers sequences are shown in Table 2 (below). The entire cassette was then cleaved from pBluescript with XbaI and BglII and ligated into the XbaI and BglII sites of the AcMNPV transfer vector pAcUW2B (Weyer et al. 1990) for generation of recombinant virus by homologous recombination. Protein-GFP reporter viruses were similarly constructed in which the membrane protein was one of: cannabinoid receptor 2 (hCR2), cytokine receptor 2B (CCR2B)), natriuretic peptide receptor C (NPR3), transient receptor potential vanilloid 4 (TRPV4), and secreted alkaline phosphatase (SEAP), (constructs not shown in FIG. 1).

The forward primer introduced restriction sites for SpeI and EcoRI and the reverse primer introduced HindIII and AgeI sites. The PCR product was gel isolated using a QiaQuick gel extraction kit (Qiagen Inc., Valencia, Calif.), cleaved with HindIII and SpeI and cloned into BluescriptSK+ (Stratagene, La Jolla, Calif.) (FIG. 1). GFP was amplified from pEGFP-1 (Clontech, Mountain View, Calif.) using primers GFPF and GFPR (Table 2), isolated as described for NTSR1, cleaved with AgeI and HindIII, and cloned in frame with NTSR1 in Bluescript SK+. The resulting plasmid was sequenced to verify the sequences and confirm that the coding sequences were in frame. Primers used for sequencing were T3 and T7 (Stratagene, La Jolla, Calif.) and gene specific primers GFPseq, NTSR1$_1$, NTRS1$_2$, and NTSR1$_3$ (Table 2). AcMNPV p10 and ie-1 promoters were PCR amplified using primers Acp10F. and Acp10R, and with primers Acie-1F and Acie-1R, respectively (Table 2). Following gel purification each promoter PCR product was cleaved with XbaI and EcoRI and cloned in front of the NTSR1/GFP fusion in pBluescript SK+. Then each promoter fusion-protein construct was cleaved from Bluescript SK+with XbaI and BglII and ligated into pAcUW2B (Weyer et al. 1990). The resulting transfer vectors along with Bsu36I cleaved Baculogold DNA (Pharmingen, BD Biosciences, San Jose, Calif.) were co-transfected into Sf21 cells using Cellfectin (Invitrogen, Carlsbad, Calif.) to generate recombinant viruses by homologous recombination (O'Reilly et al. 1992). Recombinant viruses, Pie1-NTSR1-GFP or P10-NTSR1-GFP, were selected as white polyhedrin (polh) positive plaques against a background of blue, polh-non-recombinant viruses in the presence of 120 µg/ml X-gal.

Flow Cytometry and Confocal Fluorescent Microscope Examination. Sf21, TnT4, and Hi-5 cells, $5 \times 10^5$ cells/well were placed in 6-well plates and mock-infected or infected with Pie1-NTSR1-GFP or P10-NTSR1-GFP (MOI=10) for 1 hour the following day. Then the virus was aspirated and replaced with fresh media. Cells were conducted to Flow Cytometry (BD Bioscience Vantage SE) to examine the percentage of GFP positive cells and the average intensity of GFP fluorescent at 24 h and 48 h after infection. Data were collected and analyzed using BD CellQuest. Sf21 and TnT4 cells were infected as described and analyzed by Confocal Fluorescent Microscope (Olympus Fluoview 100) at 24 h and 48 h after infection. Data were collected and analyzed using Olympus Fluoview 100 software.

Secreted alkaline phosphatase (SEAP) assay. Sf21 or TnT4 cells were seeded at $5 \times 10^5$ cells per 35 mm dish and used for infection the following day. Cells were mock infected or infected at MOI=10 for 1 h by rAcMNPV-SEAP virus (Davis et al. 1992) (kindly provided by P. Wang, Cornell U.), which contains a SEAP gene expressed from the polh promoter. Cells and media were collected at 24, 48, 72, 96, 120, or 144 h after infection. For each time point, three replicates of cells were infected and collected. Then cells were spun down and half of the supernatant was removed to a new tube. Cells were then resuspended in the remaining media and sonicated for 10 sec to disrupt the cells. Both the cell lysates and supernatant media were heated to 65° C. for 5 min and stored at −20° C. until assayed. SEAP activity was determined by a colorimetric assay using p-nitrophenol phosphate (Sigma P-4744) as substrate using a previous described protocol (Cullen and Malim 1992), modified to measure a single time point. Prewarmed cell lysates or medium samples in lx SEAP buffer were incubated with substrate for 10 minutes and the reactions were stopped by the addition of 4 volumes of 1M NaOH and the absorbance read at 405 nm. Total cell proteins were determined using Bradford method with a kit from Biorad (Richmond, Calif.) and the expression of SEAP was calculated as international units (IU)/mg cell protein.

Example 2

Cell Line Production

Cell lines were established from minced whole *T. ni* embryos in TC100 medium. TnT4 cells were obtained from one of eight flasks initiated in early 2005. These cells grew well and were split two months after initial seeding. Cells were split twice more at two-month intervals and subsequently at one-month intervals. One year after initiation, at passage number 15, cells were split once a week, at a split ratio of 1:4. Two years after initiation cells were subcultured twice a week at a split ratio of 1:14. TnT4 was selected for further characterization and development because it expressed the NTSR1-GFP-fusion protein, grew rapidly, and adapted readily to spinner culture. In plates, the TnT4 cells displayed variable morphologies including a small number of round cells and many cells with extended filipodia exhibiting diverse morphology (FIG. 2), but formed a contiguous sheet-like monolayer when confluent. When transferred to spinner culture the cells occasionally formed aggregates but if stirred at sufficient speed in suspension they were maintained as single cells. For verification purposes DNA was extracted from the cells and DAF analysis performed as previously described (McIntosh et al. 1996). The DAF profile of TnT4 cells was distinct from that of Sf21 (FIG. 3).

Example 3

Cell Growth and Virus Production

Cell growth rate was determined by counting cells, grown in tissue culture plates, at 24 h intervals (FIG. 4A). Calculated average cell doubling time was 21 hours. Production of AcMNPV budded virus in TnT4 cells was compared with that of Sf21 cells over time (FIG. 4B). TnT4 cells produced less BV than Sf21 cells over a 72 h period. There was also a delay in initial BV production in TnT4 cells compared to Sf21 cells (FIG. 4B, compare 12 and 24 h time points).

Example 4

Protein Expression

TnT4 protein expression was compared to that of Sf21 and Hi-5 cells by infecting cells with P10-NTSR1-GFP or Pie1-NTSR1-GFP, recombinant AcMNPV each expressing a G-protein coupled receptor EGFP-fusion protein. Expression levels at various times post-infection (pi) were compared by flow cytometry analysis of fluorescence (Table 1). Cellular localization and relative GFP expression within Sf21 and TnT4 cell populations were analyzed by confocal microscopy (FIGS. 5 and 6). All of the cells had low autofluorescence, see mock-infected cells (mock, Table 1, FIGS. 5A and 6A). Flow cytometry analysis indicated differences in promoter strength and utilization among Sf21, Tn4, and Hi-5 cells at 24 h pi. At 24 h pi the percentage of cells expressing NTSR1-GFP from the ie-1 promoter was considerably higher in TnT4 than in Sf21 cells (Compare FIGS. 5B and 6B, Table 1). In addition the fluorescent intensity of the TnT4 GFP+ cells was significantly greater than the Sf21 cells (p=0.028). Hi-5 cells had a higher percentage of fluorescing cells than either Sf21 or TnT4, and similar fluorescent intensity as TnT4 cells. At 24 h pi, while the percentage of cells expressing NTSR1-GFP from the P10 promoter was slightly higher in Sf21 than in TnT4 cells, the fluorescence intensity was approximately two-fold more (Compare FIGS. 5C and 6C, Table 1). At 24 h pi, Hi-5 cells expressing NTSR1-GFP from the P10 promoter was higher than either Sf21 or TnT4 cells.

At 48 h pi most cells (greater than 90%) of all cell lines were infected and expressing NTSR1-GFP from both promoters (Table 1; FIGS. 5C, 5E, 6C and 6E). Fluorescent intensity was slightly lower in both TnT4 and Hi-5 cells than in Sf21 cells when NTSR1-GFP was expressed from the ie-1 promoter, but twice that of Sf21 cells when expressed from the P10 promoter (Table 1). Fluorescent intensity of GFP+ cells expressed from the p10 promoter was significantly higher than Sf21 cells for both TnT4 (p=0.004) and Hi-5 (p=0.03).

Example 5

Secreted Glycoprotein Production

Infection with a recombinant AcMNPV expressing human placental secreted alkaline phosphatase (SEAP) (Davis et al. 1992) has been used to assess the ability of insect cells to express and glycosylate secretory proteins (Davis et al. 1992; Palomares et al. 2003). To further characterize protein expression in TnT4 cells the inventors compared SEAP production between Sf21 and TnT4 cells infected with rAcSEAP, which expresses SEAP from the AcMNPV polh promoter. SEAP activity in cell-free culture supernatants and cell lysates was analyzed (FIG. 7). At 24 h pi, significantly more SEAP activity was detected in both supernatants and cell lysates from infected Sf21 than from TnT4 cells (p=0.01). At all other times there were no statistical differences in SEAP activity between the two cell lines. However there were trends towards higher levels of SEAP activity in cell lysates from TnT4 and in supernatants from Sf21 cells at later times pi.

Example 6

Methods for hCR2, CCR2B, NPR3 and TRPV4 Membrane Proteins

Expression levels of hCR2, CCR2B, NPR3 and TRPV4 membrane proteins were compared by fluorescent intensity of the membrane protein/green fluorescent fusion-protein captured using a Coolsnaps camera mounted on a Nikon Eclipse inverted fluorescent microscope. Briefly, $2.5 \times 10^5$ cells were laid down to each well of the 12-well plate and cells were infected with the virus at MOI of 5. For each well, eight different views of the cells were selected randomly and pictures were taken under the same exposure time (250 ms) 24 h, 48 h and 72 h post infection. The same threshold was set up to get rid of the background and the average intensity of the GFP/area was measured by Metamorph V7.1 software (Molecular Devices). Data are shown from three independent experiments for each virus infected cell line (see, Table 3 and FIGS. 9A-9D). All constructs were made by inserting the Green Fluorescent Protein (GFP) coding sequence in frame with the C-terminus of the membrane protein coding sequence at the Autographa californica nucleopolyhedrovirus (AcMNPV) polyhedron gene locus, under control of the p10 promoter. The DNA sequences beginning with the start codon and ending with the stop codon for each of the hCR2, CCR2B, NPR3 and TRPV4 membrane proteins are identified as SEQ ID NOs. 18, 20, 22, and 23, respectively. All constructs included the membrane protein start codon and had the GFP coding sequence immediately following the last codon before the stop codon of the membrane protein. The recombinant viruses were used to infect insect cells and fluoresent intensity was measured as described above.

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the spirit and scope of the invention. Such modifications, equivalent variations and additional embodiments are also intended to fall within the scope of the appended claims.

REFERENCES

Akermoun, M.; Koglin, M.; Zvalova-Iooss, D.; Folschweiller, N.; Dowell, S. J. Gearing, K. L. Characterization of 16 human G protein-coupled receptors expressed in baculovirus-infected insect cells. Protein Expr. Purif., 44: 65-74; 2005.

Becker, G. W.; Miller, J. R.; Kovacevic, S.; Ellis, R. M.; Louis, A. I.; Small, J. S.; Stark, D. H.; Roberts, E. F.; Wyrick, T. K.; Hoskins, J.; Chiou, X. G.; Sharp, J. D.; McClure, D. B.; Riggin, R. M. Kramer, R. M. Characterization by Electrospray Mass-Spectrometry of Human Ca2+-Sensitive Cytosolic Phospholipase-a(2) Produced in Baculovirus-Infected Insect Cells. Bio-Technology, 12: 69-74; 1994.

Chai, H.; AlRubeai, M.; Chua, K. L.; Oh, S. K. W. Yap, M. G. S. Insect cell line dependent gene expression of recombinant human tumor necrosis factor-beta. Enzyme Microb. Technol., 18: 126-132; 1996.

Chen, C. J. Thiem, S. M. Differential infectivity of two *Autographa californica* nucleopolyhedrovirus mutants on three permissive cell lines is the result of lef-7 deletion. Virology, 227: 88-95; 1997.

Clem, R. J.; Fechheimer, M. Miller, L. K. Prevention of Apoptosis by a Baculovirus Gene During Infection of Insect Cells. Science, 254: 1388-1390; 1991.

Cullen, B. R. Malim, M. H. Secreted Placental Alkaline-Phosphatase as a Eukaryotic Reporter Gene. Methods in Enzymology, 216: 362-368; 1992.

Davis, T. R.; Trotter, K. M.; Granados, R. R. Wood, H. A. Baculovirus Expression of Alkaline-Phosphatase as a Reporter Gene for Evaluation of Production, Glycosylation and Secretion. Bio-Technology, 10: 1148-1150; 1992.

Davis, T. R.; Wickham, T. J.; McKenna, K. A.; Granados, R. R.; Shuler, M. L. Wood, H. A. Comparative Recombinant Protein-Production of 8 Insect-Cell Lines. In Vitro Cell. Dev. Biol.-Anim., 29A: 388-390; 1993.

Gaw, Z.-Y.; Liu, N. T. Zia, T. U. Tissue culture methods for cultivation of virus grasserie. Acta Virol., 3 (Suppl.): 55-60; 1959.

Grace, T. Establishment of four strains of cells from insect tissues grown in vitro. Nature (London), 195: 788-789; 1962.

Granados, R. R.; Li, G. X.; Derksen, A. C. G. McKenna, K. A. A New Insect-Cell Line from Trichoplusia Ni (Bti-Tn-5b1-4) Susceptible to Trichoplusia Ni Single Enveloped Nuclear Polyhedrosis-Virus. J. Invertebr. Pathol., 64: 260-266; 1994.

Grisshammer, R. Tate, C. G. Overexpression of Integral Membrane-Proteins for Structural Studies. Quarterly Reviews of Biophysics, 28: 315-422; 1995.

Grunewald, S.; Haase, W.; Reilander, H. Michel, H. Glycosylation, palmitoylation, and localization of the human D-2S receptor in Baculovirus-infected insect cells. Biochemistry, 35: 15149-15161; 1996.

Hink, W. F. A Serum-Free Medium for the Culture of Insect Cells and Production of Recombinant Proteins. In Vitro Cellular & Developmental Biology, 27: 397-401; 1991.

Hollister, J.; Grabenhorst, E.; Nimtz, M.; Conradt, H. Jarvis, D. L. Engineering the Protein N-Glycosylation Pathway in Insect Cells for Production of Biantennary, Complex N-Glycans. Biochemistry, 41: 15093-15104; 2002.

Kuchler, R. J. Biochemical Methods in Cell Culture and Virology. Stroudsburg: Dowden, Hutchinson & Ross, Inc. 1977.

Lu, A. Miller, L. K. Species-specific effects of the hcf-1 gene on baculovirus virulence. J. Virol., 70: 5123-5130; 1996.

Lynn, D. E. Development and characterization of insect cell lines. Cytotechnology, 20: 3-11; 1996.

Lynn, D. E. Novel techniques to establish new insect cell lines. In Vitro Cellular & Developmental Biology-Animal, 37: 319-321; 2001.

Massotte, D. G protein-coupled receptor overexpression with the baculovirus-insect cell system: a tool for structural and functional studies. Biochim. Biophys. Acta-Biomembr., 1610: 77-89; 2003.

McCusker, E. C.; Bane, S. E.; O'Malley, M. A. Robinson, A. S. Heterologous GPCR expression: A bottleneck to obtaining crystal structures. Biotechnol. Prog., 23: 540-547; 2007.

McIntosh, A. H.; Grasela, J. J, Matteri, R. L. Identification of insect cell lines by DNA amplification fingerprinting (DAF). Insect Mol. Biol., 5: 187-195; 1996.

McKenna, K. A.; Hong, H. Z.; vanNunen, E. Granados, R. R. Establishment of new *Trichoplusia ni* cell lines in serum-free medium for Baculovirus and recombinant protein production. J. Invertebr. Pathol., 71: 82-90; 1998.

Ng, G. Y. K.; George, S. R.; Zastawny, R. L.; Caron, M.; Bouvier, M.; Dennis, M. Odowd, B. F. Human Serotonin(1b) Receptor Expression in Sf9 Cells—Phosphorylation, Palmitoylation, and Adenylyl-Cyclase Inhibition. Biochemistry, 32: 11727-11733; 1993.

Ng, G. Y. K.; Odowd, B. F.; Caron, M.; Dennis, M.; Brann, M. R. George, S. R. Phosphorylation and Palmitoylation of the Human D2 (L) Dopamine-Receptor in Sf9 Cells. J. Neurochem., 63: 1589-1595; 1994.

O'Reilly, D. R.; Miller, L. K. Luckow, V. Baculovirus Expression Vectors: A Laboratory Manual. New York: W. H. Freeman and Company. 1992.

Ogonah, O. W.; Freedman, R. B.; Jenkins, N.; Patel, K. Rooney, B. C. Isolation and characterization of an insect cell line able to perform complex N-linked glycosylation on recombinant proteins. Bio-Technology, 14: 197-202; 1996.

Palomares, L. A.; Joosten, C. E.; Hughes, P. R.; Granados, R. R. Shuler, M. L. Novel insect cell line capable of complex N-glycosylation and sialylation of recombinant proteins. Biotechnol. Prog., 19: 185-192; 2003.

Sarramegna, V.; Talmont, R.; Demange, P. Milon, A. Heterologous expression of G-protein-coupled receptors: comparison of expression systems from the standpoint of large-scale production and purification. Cellular and Molecular Life Sciences, 60: 1529-1546; 2003.

Smith, G. E.; Ju, G.; Ericson, B. L.; Moschera, J.; Lahm, H. W.; Chizzonite, R.

Summers, M. D. Modification and Secretion of Human Interleukin-2 Produced in Insect Cells by a Baculovirus Expression Vector. Proceedings of the National Academy of Sciences of the United States of America, 82: 8404-8408; 1985.

Vaughn, J. L.; Goodwin, R. H.; Tompkins, G. J. McCawley, P. Establishment of 2 Cell Lines from Insect Spodoptera-Frugiperda (Lepidoptera-Noctuidae). In Vitro-Journal of the Tissue Culture Association, 13: 213-217; 1977.

Weyer, U.; Knight, S. Possee, R. D. Analysis of Very Late Gene-Expression by Autographa-Californica Nuclear Polyhedrosis-Virus and the Further Development of Multiple Expression Vectors. J. Gen. Virol., 71: 1525-1534; 1990.

Wickham, T. J.; Davis, T.; Granados, R. R.; Shuler, M. L. Wood, H. A. Screening of Insect Cell-Lines for the Production of Recombinant Proteins and Infectious Virus in the Baculovirus Expression System. Biotechnol. Prog., 8: 391-396; 1992.

Zavodzky, P. Cseh, S. Production of multidomain complement glycoproteins in insect cells. Cytotechnology, 20: 279-288; 1996.

Zhao, Y. Sane, D. C. Expression of a Recombinant Baculovirus for Vitronectin in Insect Cells—Purification, Characterization of Posttranslational Modifications and Functional-Studies of the Recombinant Protein. Arch. Biochem. Biophys., 304: 434-442; 1993.

What is claimed is:

1. An isolated *Trichoplusia ni* cell, which is not infected with a nodavirus, wherein a sample of said cell has been deposited as ATCC Accession No. PTA-9384.

2. The cell of claim 1 further including a baculovirus expression vector.

3. The cell of claim 2 wherein the vector carries a heterologous oligonucleotide that encodes a polypeptide.

4. The cell of claim 3 wherein the oligonucleotide is selected from the oligonucleotides having SEQ ID NOs. 1 and 16-23, or an oligonucleotide with at least 90-95% sequence identity to any of SEQ ID NOs. 1 and 16-23.

5. The cell of claim 3 wherein the polypeptide is a membrane protein.

6. The cell of claim 5 wherein the membrane protein is a G-protein coupled receptor.

7. The cell of claim 5 wherein the polypeptide is selected from the group consisting of human neurotensin receptor 1 (NTSR1), human cannabinoid receptor 2 (hCR2), cytokine receptor 2B (CCR2B), natriuretic peptide receptor C (NPR3), transient receptor potential vanilloid 4 (TRPV4), and conservative amino acid substitution variants thereof that have at least 95% sequence identity therewith.

8. The cell of claim 7 wherein the polypeptide is NTSR1, or a conservative amino acid substitution variant thereof that has at least 95% sequence identity therewith.

9. The cell of claim 3 wherein the nucleotide encodes a fusion protein.

10. The cell of claim 9 wherein the encoded fusion protein includes a protein operably linked with a marker protein.

11. The cell of claim 10 wherein the protein is NTSR1 and the marker protein is green fluorescent protein.

12. A method of producing a polypeptide comprising the steps of:
   a) providing the cell of claim 3;
   b) growing the cell such that the polypeptide is expressed; and
   c) isolating the expressed polypeptide from the cell.

13. The method of claim 12 wherein the polypeptide is a membrane protein.

14. The method of claim 13 wherein the membrane protein is a G-protein coupled receptor.

15. The method of claim 13 wherein the membrane protein is selected from the group consisting of NTSR1, hCR2, CCR2B, NPR3, TRPV4, and conservative amino acid substitution variants thereof that has at least 95% sequence identity therewith.

16. The method of claim 15 wherein the membrane protein is NTSR1.

17. The cell of claim 3 wherein the polypeptide is expressed at higher levels than the polypeptide is expressed in Sf21 cells.

18. The method of claim 12 wherein the cell is not infected with a nodavirus.

19. The method of claim 12 wherein the polypeptide is expressed at higher levels than the polypeptide is expressed in Sf21 cells.

* * * * *